(12) United States Patent
Wu et al.

(10) Patent No.: US 12,414,827 B2
(45) Date of Patent: Sep. 16, 2025

(54) SURGICAL EXECUTION APPARATUS AND SURGICAL ASSISTANCE DEVICE

(71) Applicant: ROBGENIX MEDICAL PTE. LTD., Singapore (SG)

(72) Inventors: Gang Wu, Shanghai (CN); Cunwang Ge, Shanghai (CN); Hao Chen, Shanghai (CN)

(73) Assignee: ROBGENIX MEDICAL PTE. LTD., Singapore (SG)

( * ) Notice: Subject to any disclaimer, the term of this patent is extended or adjusted under 35 U.S.C. 154(b) by 0 days.

(21) Appl. No.: 19/051,000

(22) Filed: Feb. 11, 2025

(65) Prior Publication Data

US 2025/0204997 A1   Jun. 26, 2025

Related U.S. Application Data

(63) Continuation of application No. PCT/CN2024/140574, filed on Dec. 19, 2024.

(30) Foreign Application Priority Data

Dec. 20, 2023  (CN) .......................... 202311773175.1

(51) Int. Cl.
   *A61B 34/30*    (2016.01)
   *A61B 17/00*    (2006.01)

(52) U.S. Cl.
   CPC ........ *A61B 34/30* (2016.02); *A61B 17/00234* (2013.01); *A61B 2017/00243* (2013.01); *A61B 2034/305* (2016.02)

(58) Field of Classification Search
   CPC .............. A61B 34/30; A61B 17/00234; A61B 2017/00243; A61B 2034/305
   See application file for complete search history.

(56) References Cited

FOREIGN PATENT DOCUMENTS

| CN | 107260310 A | 10/2017 |
| CN | 110720987 A | 1/2020 |
| CN | 219148062 U | 6/2023 |
| CN | 117883128 A | 4/2024 |
| WO | WO 2023/061184 A1 | 4/2023 |

OTHER PUBLICATIONS

Written Opinion and International Search Report mailed Apr. 7, 2025 in International Application No. PCT/CN2024/140574, with English translation, 14 pages.

*Primary Examiner* — Scott Luan

(74) *Attorney, Agent, or Firm* — Nixon & Vanderhye P.C.

(57) ABSTRACT

The present disclosure relates to the field of medical device technology, and specifically discloses a surgical execution apparatus and a surgical assistance device, the apparatus comprising a transmission cabin and a power cabin, the transmission cabin comprising a chassis assembly and first to third adapter transmission assemblies movable relative to the chassis assembly, the first to third adapter transmission assemblies comprising first to third transmission modules detachably connected to first to third adapter assemblies respectively; the power cabin being in transmission connection to the transmission cabin and configured to drive the first to third adapter assemblies via the first to third transmission modules. The apparatus enables more precise, stable and safe surgical execution operations through refined improvements in the transmission cabin.

17 Claims, 31 Drawing Sheets

SURGICAL EXECUTION APPARATUS AND SURGICAL ASSISTANCE DEVICE

This application is a continuation of International Application No. PCT/CN2024/140574, filed on Dec. 19, 2024, which claims the priority to Chinese Patent Application No. CN202311773175.1 filed on Dec. 20, 2023, and entitled "SURGICAL EXECUTION APPARATUS AND SURGICAL ASSISTANCE DEVICE", the entire disclosure of which is incorporated by reference herein.

TECHNICAL FIELD

The present disclosure relates to the field of medical device technology, and in particular to a surgical execution apparatus and a surgical assistance device.

BACKGROUND

Minimally invasive valve repair surgery is an advanced surgical approach for treating valvular heart diseases including those of mitral and tricuspid valves. Taking mitral valve repair surgery as an example, the surgery is primarily performed via a transcatheter method, which can reduce surgical trauma and shorten recovery time. Specifically, the surgeon delivers the catheter to the mitral valve site through the femoral vein or via an apical puncture, where specialized instruments are used to repair the damaged valve. This surgical approach offers several advantages, including minimal trauma, reduced bleeding, and faster recovery, as well as effectively lowered incidence of postoperative complications.

Traditional minimally invasive mitral valve repair surgery requires surgeons to manually operate invasive mitral valve repair instruments with their both hands, in order to for example hold handles, manipulate knobs, extend or retract the handles and push or pull levers, to complete the surgical procedures. In most cases, the surgical procedures need to be performed under the fluoroscopic guidance, thereby necessitating the surgeons to manually manipulate the instruments while wearing heavy lead protective gears for prolonged time, which significantly impacts the quality of surgeons' diagnosis and treatment activities, as well as their physical stamina and health, especially for experienced elderly or female surgeons. Certain complex surgical techniques or instruments, due to their high operational difficulty, demand a high level of technical skill and clinical experience from surgeons, and requires a relatively long learning curve for surgeons, which to some extent restricts the development of surgical techniques or the clinical application of instruments.

SUMMARY

The present disclosure is directed to providing a surgical execution apparatus and a surgical assistance device for facilitating valve repair surgery for surgeons, so as to improve the operational accuracy and efficiency of valve repair instruments, reduce the physical demands on surgeons, and shorten the learning curves required for surgeons to master complex surgical techniques.

To achieve this objective, the present disclosure provides the following technical solutions:

A surgical execution apparatus includes a transmission cabin and a power cabin, the transmission cabin including a chassis assembly and a first adapter transmission assembly, a second adapter transmission assembly and a third adapter transmission assembly that are movable relative to the chassis assembly, and the power cabin being in transmission connection to the transmission cabin, where the first adapter transmission assembly is slidably attached to the chassis to slide along an adjustment direction that is parallel to a lengthwise direction of the transmission cabin, the second adapter transmission assembly is slidably attached to the first adapter transmission assembly to slide along the adjustment direction, and the third adapter transmission assembly is slidably attached to the second adapter transmission assembly to slide along the adjustment direction.

As a preferred technical solution of the surgical execution apparatus, the power cabin includes a motor assembly including an assembly frame plate and a plurality of drive motors mounted on the assembly frame plate, with output ends of the drive motors extending through the assembly frame plate; and the transmission cabin includes an axial end fixing assembly provided at one end of the first adapter transmission assembly, the axial end fixing assembly comprising a fixing end plate and input end connection assemblies extending through and rotatably connected to the fixing end plate, where the input end connection assemblies and the drive motors are equal in number, and each input end connection assembly is coaxially and detachably connected to an output end of one of the drive motors.

As a preferred technical solution of the surgical execution apparatus, the chassis assembly includes a bottom bracket and a guide rail connection plate slidably provided on the bottom bracket, and the first adapter transmission assembly includes a frame, with the axial end fixing assembly being fixed to one end of the frame, and the guide rail connection plate being fixed to the frame.

As a preferred technical solution of the surgical execution apparatus, a first trapezoidal nut is installed on the bottom bracket, and a first trapezoidal screw is rotatably connected to the guide rail connection plate to rotate around the adjustment direction, where the first trapezoidal nut is in transmission engagement with the first trapezoidal screw; and/or the second adapter transmission assembly includes a transmission support plate with a second trapezoidal nut being installed thereon, and a second trapezoidal screw is rotatably connected to the axial end fixing assembly to rotate around the adjustment direction, where the second trapezoidal nut is in transmission engagement with the second trapezoidal screw; and/or a third trapezoidal screw is rotatably connected to the transmission support plate to rotate around the adjustment direction, and the third adapter transmission assembly includes a slider connection plate with a third trapezoidal nut being installed thereon, where the third trapezoidal nut is in transmission engagement with the third trapezoidal screw.

As a preferred technical solution of the surgical execution apparatus, the first trapezoidal screw is coaxially fixed to one of the input end connection assemblies via a first cross slider coupling and one of second cross slider couplings in sequence; and/or the second trapezoidal screw is coaxially fixed to one of the input end connection assemblies via one of the second cross slider couplings; and/or the third trapezoidal screw is coaxially fixed to one of the input end connection assemblies via one of telescopic universal couplings and one of the second cross slider couplings in sequence.

As a preferred technical solution of the surgical execution apparatus, the first adapter transmission assembly includes a first transmission module including a plurality of first transmission structures, each including a first transmission shaft rotatable around the adjustment direction, with respective third cross slider couplings being coaxially fixed to both ends of the first transmission shaft, where one end of the first transmission shaft is coaxially fixed to one of the input end connection assemblies, and the other end is in transmission connection to one of first adapter output assemblies via a first bevel gear swivel.

As a preferred technical solution of the surgical execution apparatus, the second adapter transmission assembly includes a second transmission module including a plurality of second transmission structures, each including a second transmission shaft rotatable around the adjustment direction, where one end of the second transmission shaft is coaxially fixed to one of the input end connection assemblies via one of telescopic universal couplings and one of second cross slider couplings in sequence, and the other end is in transmission connection to one of second adapter output assemblies via a second bevel gear swivel.

As a preferred technical solution of the surgical execution apparatus, the third adapter transmission assembly includes a third transmission module including a plurality of third transmission structures, each including a ball spline assembly rotatable around the adjustment direction, where the ball spline assembly includes a ball spline outer shaft and a ball spline inner shaft in transmission engagement, the ball spline inner shaft being insertable into the ball spline outer shaft and coaxially fixed to one of the input end connection assemblies via a universal coupling, and the ball spline outer shaft being in transmission connection to one of third adapter output assemblies via a third bevel gear swivel.

A surgical assistance device includes a robotic arm, a first adapter assembly, a second adapter assembly, a third adapter assembly and the above-mentioned surgical execution apparatus that is detachably connected to the robotic arm, where the first adapter transmission assembly includes a first transmission module detachably connected to the first adapter assembly, the second adapter transmission assembly includes a second transmission module detachably connected to the second adapter assembly, and the third adapter transmission assembly includes a third transmission module detachably connected to the second adapter assembly; the power cabin is configured to drive the first adapter assembly via the first transmission module, drive the second adapter assembly via the second transmission module, and drive the third adapter assembly via the third transmission module.

As a preferred technical solution of the surgical assistance device, the transmission cabin further includes an operation panel provided on the chassis assembly, the operation panel being communicatively connected to the first adapter assembly, the second adapter assembly and the third adapter assembly, and configured to display parameter information of the first adapter assembly, the second adapter assembly and the third adapter assembly.

Beneficial Effects

The surgical execution apparatus individually drives the first, second, and third adapter assemblies, which can enhance the flexibility of their output motions, facilitating refined operations required for surgical techniques, thus ensuring more precise, stable and safe operations of the surgical execution apparatus. Through the split design of the transmission cabin for power transmission and the power cabin for power generation, the active components are separated from the passive components in the surgical execution apparatus, thereby not only eliminating the risk of cable breakage or wear during transmission and movement of the surgical execution apparatus and avoiding issues related to the loosening of active connectors due to prolonged use, but also improving the electromagnetic shielding performance by isolating the active components within the power cabin. The transmission structure of the transmission cabin is simple and compact, which can effectively reduce the structural size of the surgical execution apparatus, and can improve the transmission efficiency, thus contributing to more stable, accurate and reliable operations. The apparatus with above structural design also offers high scalability, allowing for the replacement of different adapters according to specific surgical technique requirements, thereby expanding the range of applicable surgical techniques. The above improvements in the surgical execution apparatus can lower the experience required for surgeons in operating surgical instruments, decrease their physical exertion, and mitigate the impact of radiation from the surgical execution apparatus on them, while facilitating the intelligent operation of minimally invasive surgical diagnosis and treatment. The surgical execution apparatus, when being used by surgeons for surgical techniques, can ensure the stability and accuracy of surgical operations, and improve efficiency thereof, thus shortening the procedure durations. The application of the surgical execution apparatus also contributes to improving the working environment for surgeons, reducing the physical demands on them, and shortening the learning curves required for them to master complex surgical techniques.

The surgical assistance device can be connected to the valve repair instrument via adapters to drive the movements of the instrument, thereby assisting surgeons in operating the valve repair instrument and complete the valve repair surgery.

Figure 1:
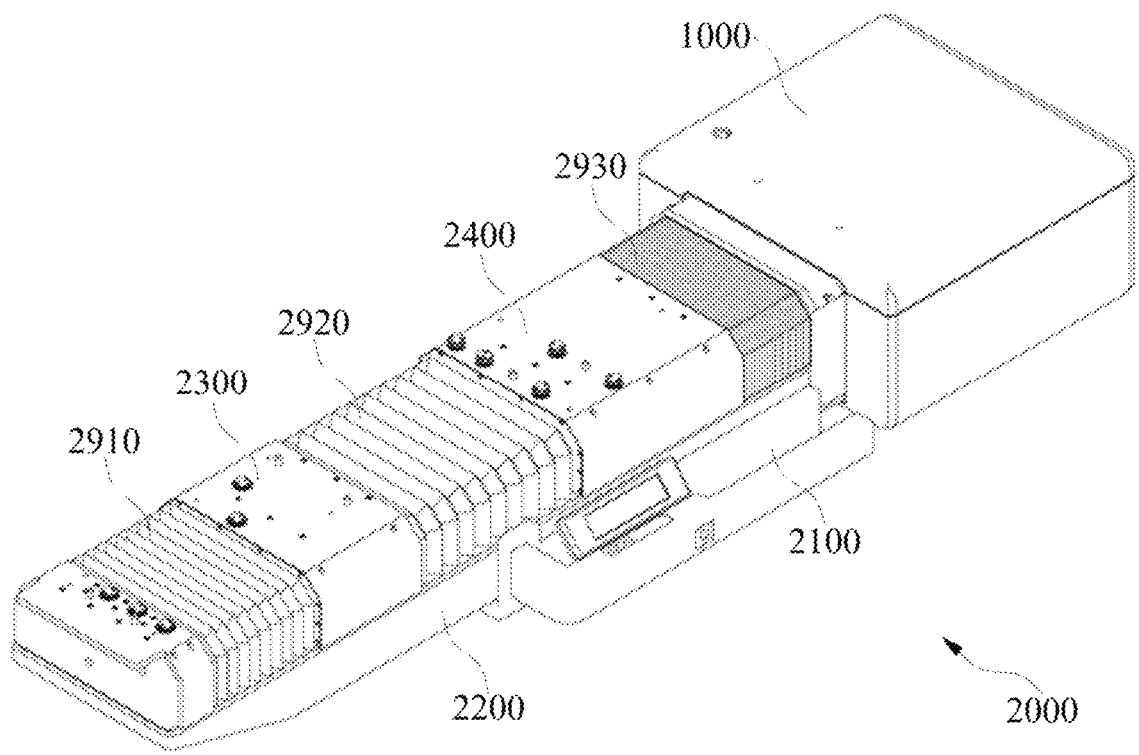
FIG. 1 is a schematic diagram of the structure of the surgical execution apparatus according to an embodiment of the present disclosure.

1000: power cabin; 1100: bottom shell; 1200: top cover; 1300: motor assembly; 1310: drive motor; 1320: assembly frame plate; 1400: driver assembly;

2000: transmission cabin; 2100: chassis assembly; 2110: bottom bracket; 2120: chassis main beam; 2121: first linear guide rail; 2122: first nut fixing seat; 2123: first trapezoidal nut; 2130: guide rail connection plate; 2131: first bearing seat; 2132: first trapezoidal screw; 2140: first cross slider coupling; 2180: L-shaped support; 2190: handle; 2191: bedside operation panel; 2200: first adapter transmission assembly; 2210: frame; 2211: second bearing seat; 2212: second linear guide; 2220: axial end assembly for first adapter assembly; 2221: output end bearing seat; 2222: output end shaft body; 2223: sixth flanged bearing; 2224: sixth elastic retaining ring; 2225: output end shaft key; 2230: first transmission unit for first adapter assembly; 2231: first adapter assembly mounting plate; 2232: first positioning pin; 2233: first bevel gear swivel; 2240: second transmission unit for first adapter assembly; 2241: three-bearing support; 2242: first transmission shaft; 2250: third cross slider coupling; 2260: axial end fixing assembly; 2261: fixing end plate; 2262: universal coupling; 2263: ball spline inner shaft; 2264: telescopic universal coupling; 2265: second cross slider coupling; 2270: input end connection assembly; 2271: first flanged bearing; 2272: first elastic retaining ring; 2273: input end connector shaft; 2274: first adapter assembly connection flange; 2275: first spring; 2276: first column head screw; 2280: long shaft output assembly for first adapter assembly; 2281: second adapter connection flange; 2282: second flanged bearing; 2283: second elastic retaining ring; 2284: long connector shaft; 2285: second spring; 2286: second column head screw; 2287: long connector bearing seat; 2290: short shaft output assembly for first adapter assembly; 2291: third adapter connection flange; 2292: third flanged bearing; 2293: third elastic retaining ring; 2294: short connector shaft; 2295: third spring; 2296: third column head screw; 2297: short connector bearing seat; 2300: second adapter transmission assembly; 2310: transmission support plate; 2311: slider fixing plate; 2312: first slider; 2320: second adapter mounting cover; 2321: second positioning pin; 2330: second adapter output assembly; 2331: fourth adapter connection flange; 2332: fourth flanged bearing; 2333: fourth elastic retaining ring; 2334: second adapter connector shaft; 2335: fourth spring; 2336: fourth column head screw; 2337: middle adapter output bearing seat; 2341: second nut fixing seat; 2342: second trapezoidal nut; 2350: trapezoidal screw unit; 2351: third trapezoidal screw; 2352: third bearing seat; 2360: dual bearing seat assembly; 2361: bearing seat body; 2362: bearing cover; 2363: fifth column head screw; 2364: first rolling bearing; 2370: second bevel gear swivel; 2380: reinforcing rib; 2400: third adapter transmission assembly; 2410: slider connection plate; 2411: second slider; 2412: second rolling bearing; 2420: third adapter mounting cover; 2421: third positioning pin; 2430: third adapter output assembly; 2431: fifth adapter connection flange; 2432: fifth flanged bearing; 2433: fifth elastic retaining ring; 2434: first three adapter connector shaft; 2435: fifth spring; 2436: fifth column screw; 2440: ball spline assembly; 2441: ball spline body; 2442: ball spline outer shaft; 2450: third bevel gear swivel; 2460: third trapezoidal nut; 2470: second trapezoidal screw; 2910: first bellows cover; 2920: second bellows cover; 2930: third bellows cover;

8000: mitral valve repair instrument; 8100: guide wire; 8200: sheath; 8300: catheter assembly; 8310: outer catheter; 8320: middle catheter; 8330: inner catheter; 8340: clip; 8400: first driving handle; 8500: second driving handle; 8600: third driving handle; 8700: first adapter assembly; 8800: second adapter assembly; 8900: third adapter assembly;

9000: human body; 9100: right femoral vein; 9200: left femoral vein; 9300: inferior vena cava; 9400: descending aorta; 9500: superior vena cava; 9600: right jugular vein; 9700: left jugular vein; 9800: subclavian vein; 9900: heart; 9910: right atrium; 9920: atrial septum; 9930: left atrium; 9940: mitral valve; 9950: left ventricle.

DETAILED DESCRIPTION

The technical solution of the present disclosure will be described below clearly and completely with reference to the accompanying drawings. It should be understood the embodiments described herein are only a part of the possible embodiments of the present disclosure, and do not represent all possible embodiments. Based on the embodiments of the present disclosure, any other embodiments obtained by a person of ordinary skill in the art without any creative effort are also within the scope of protection of the present disclosure.

In the description of the present disclosure, it should be noted that the terms such as "center", "upper", "lower", "left", "right", "vertical", "horizontal", "inner", "outer" indicate the relative positions or orientations based on the those as shown in the drawings, for the purpose of concise description of the present disclosure only, rather than indicating or implying that the device or element referred to must have a particular orientation, or be constructed and operated in a particular orientation. Therefore, these terms should not be interpreted as limitations to the present disclosure. Furthermore, the terms such as "first" and "second" are for a distinguishing purpose only, and should not be construed as indicating or implying relative importance. Accordingly, the terms "first position" and "second position" refer to two distinct positions. When a first feature is described as being "above", "over" and "on" a second feature, it includes both the case where the first feature is directly above the second feature and the case where the first feature is obliquely above the second feature, or simply indicates that the first feature is at a higher level than the second feature. When the first feature is described as "below", "under" and "beneath" the second feature, it includes both the case where the first feature is directly below the second feature and the case where the first feature is obliquely below the second feature, or simply indicates that the first feature is at a lower level than the second feature.

In the description of the present disclosure, it should be noted that, unless otherwise clearly specified and limited, the terms such as "install", "connect" and "couple" should be comprehended in a broad sense, and may be comprehended as, for example, fixed or detachable connection, or integrated connection; a mechanical or electrical connection; a direct connection or an indirect connection through an intermediate medium; or a communication between interiors of two elements. The specific meanings of the above terms in the present disclosure may be understood by a person of ordinary skill in the art according to specific context.

The embodiments of the present disclosure are described below in detail, and examples of the embodiments are shown in the accompanying drawings, in which the same or similar reference numerals throughout represent the same or similar elements or elements having the same or similar functions. The embodiments described below with reference to the accompanying drawings are exemplary and are for the purpose of explaining the present disclosure only, and should not be construed as limiting the present disclosure.

Figure 2:
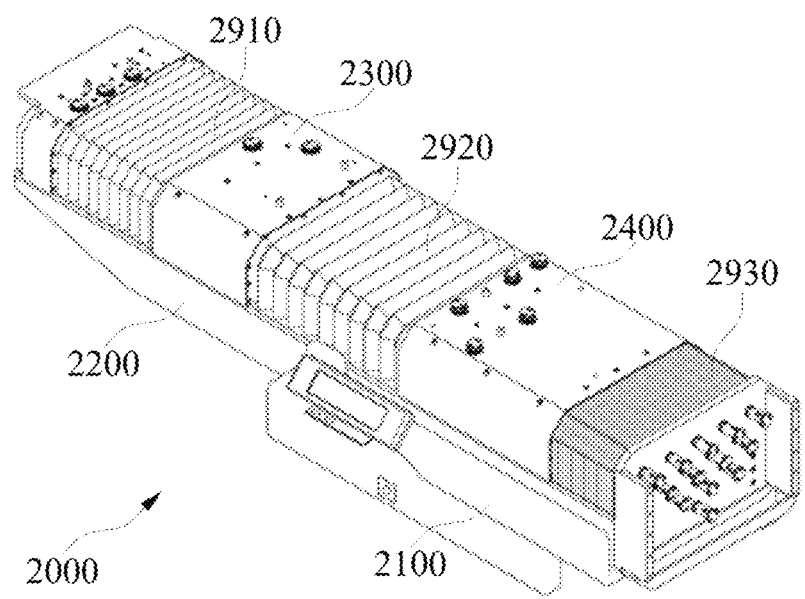
FIG. 2 is a schematic diagram of the structure of the transmission cabin according to an embodiment of the present disclosure.
Figure 3:
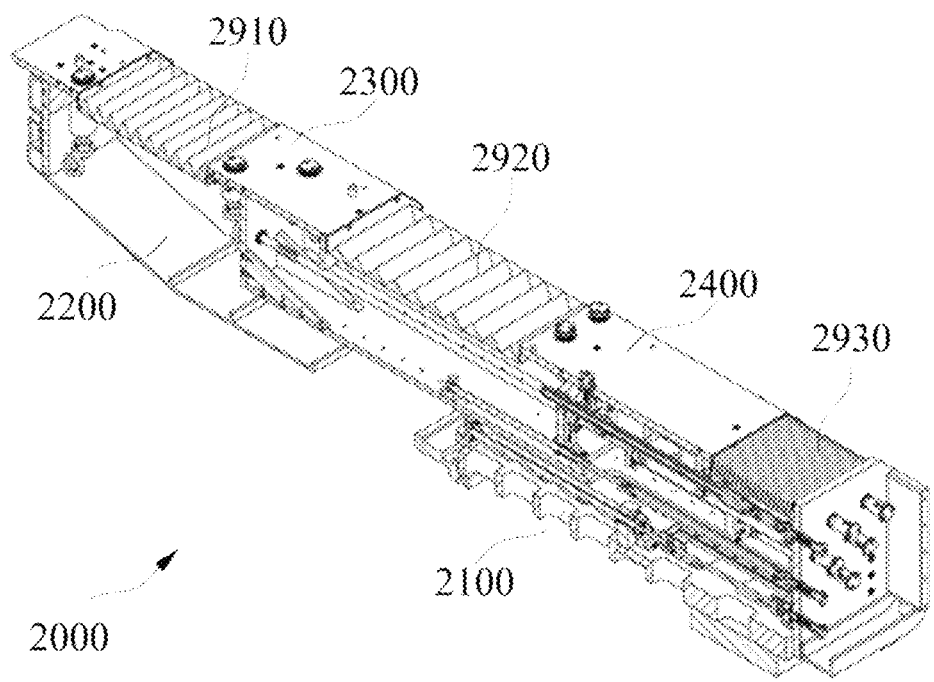
FIG. 3 is a cross-sectional view of the transmission cabin according to an embodiment of the present disclosure.
Figure 4:
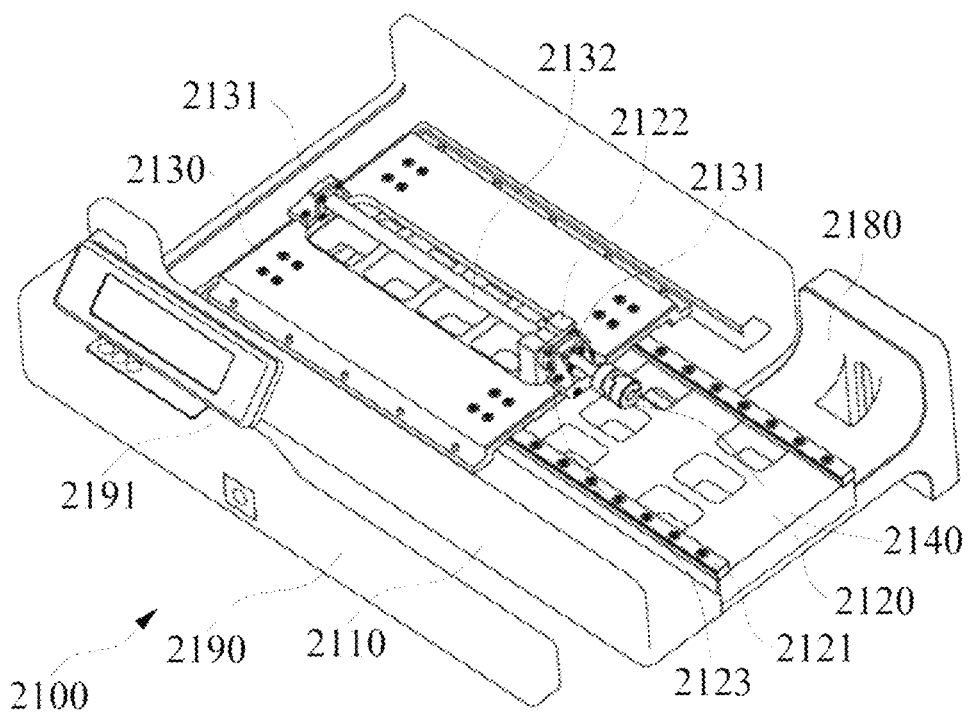
FIG. 4 is a schematic diagram of the structure of the chassis assembly according to an embodiment of the present disclosure.
Figure 5:
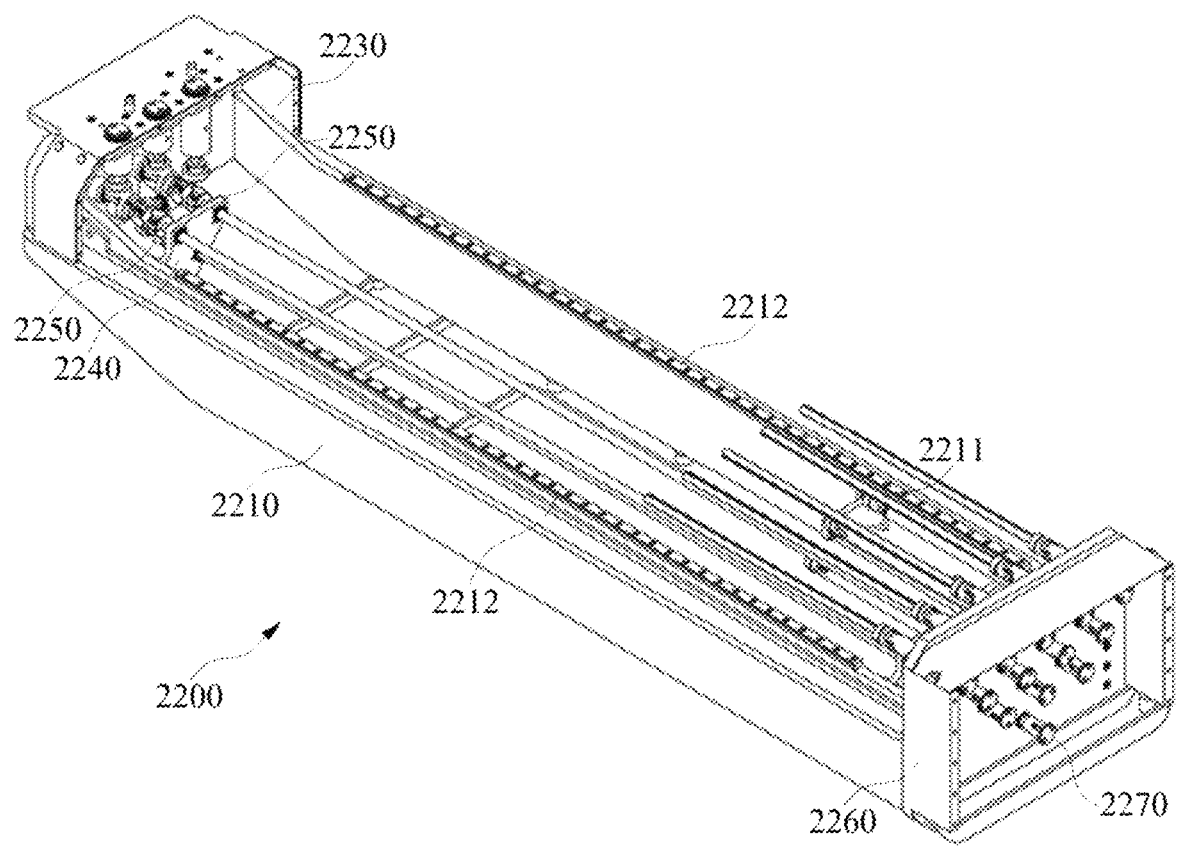
FIG. 5 is a schematic diagram of the structure of the first adapter transmission assembly according to an embodiment of the present disclosure.
Figure 6:
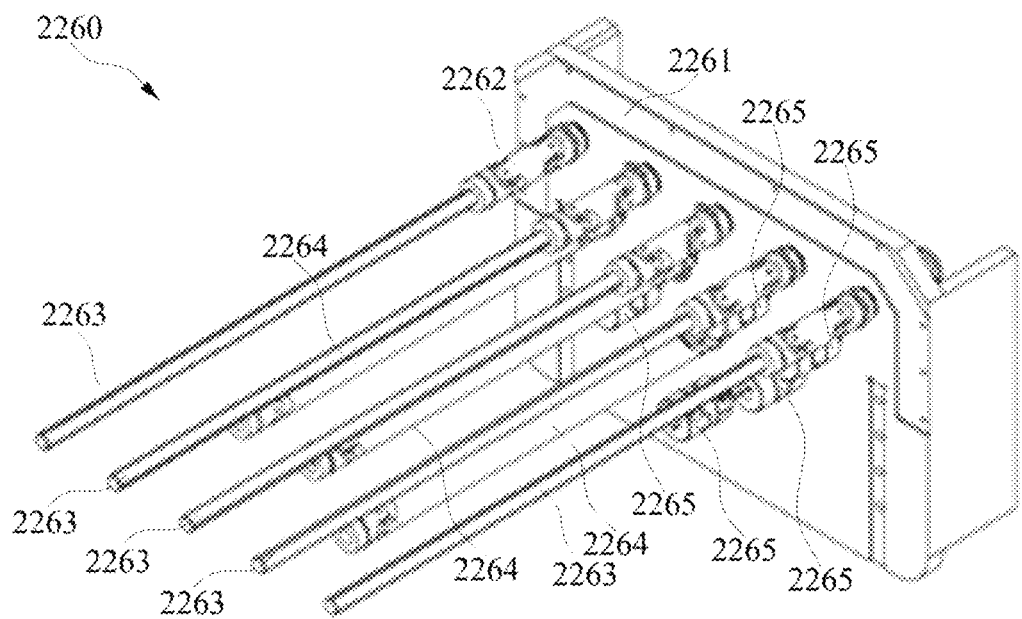
FIG. 6 is a schematic diagram of the structure of the axial end fixing assembly according to an embodiment of the present disclosure.
Figure 7:
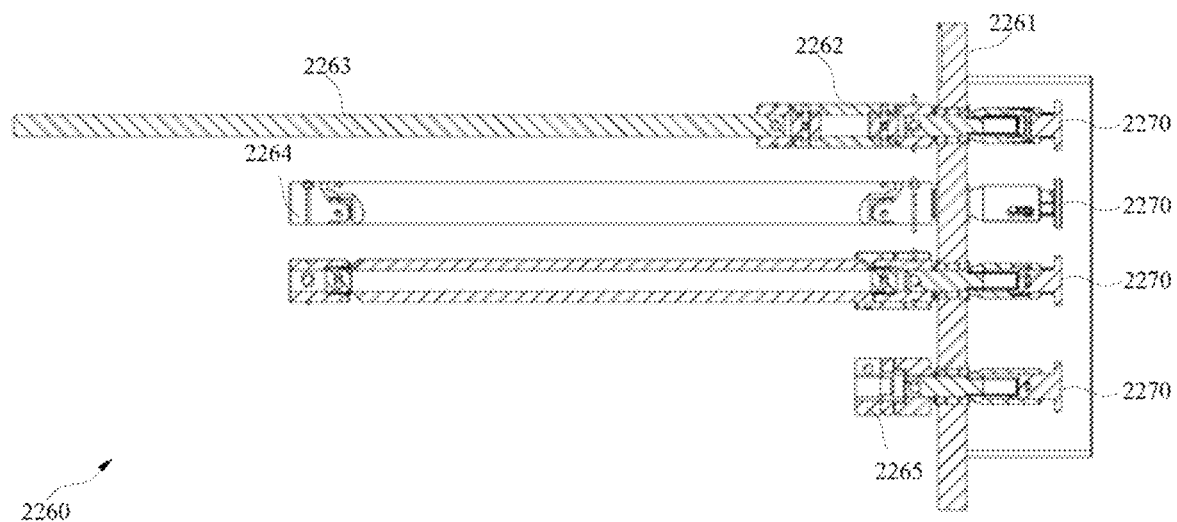
FIG. 7 is a cross-sectional view of the axial end fixing assembly according to an embodiment of the present disclosure.
Figure 8:
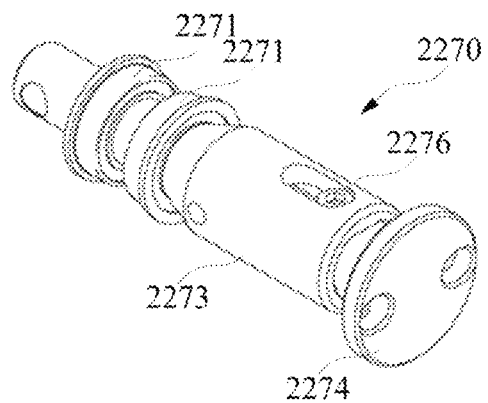
FIG. 8 is a schematic diagram of the structure of the input end connection assembly according to an embodiment of the present disclosure.
Figure 9:
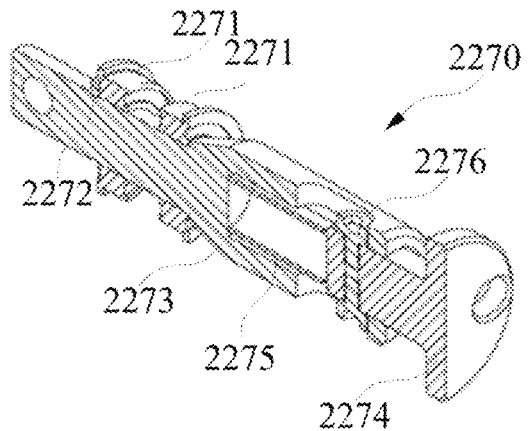
FIG. 9 is a cross-sectional view of the input end connection assembly according to an embodiment of the present disclosure.
Figure 10:
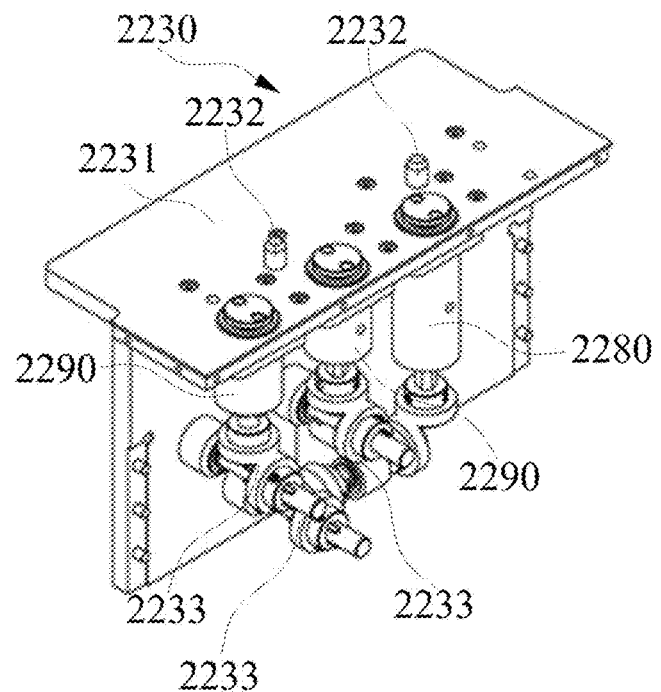
FIG. 10 is a schematic diagram of the structure of the first transmission unit for first adapter assembly according to an embodiment of the present disclosure, viewed from a first perspective.
Figure 11:
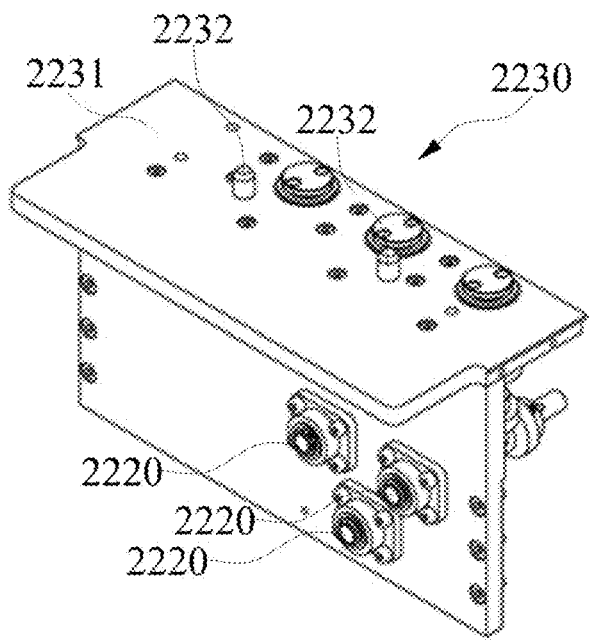
FIG. 11 is a schematic diagram of the structure of the first transmission unit for first adapter assembly according to an embodiment of the present disclosure, viewed from a second perspective.
Figure 12:
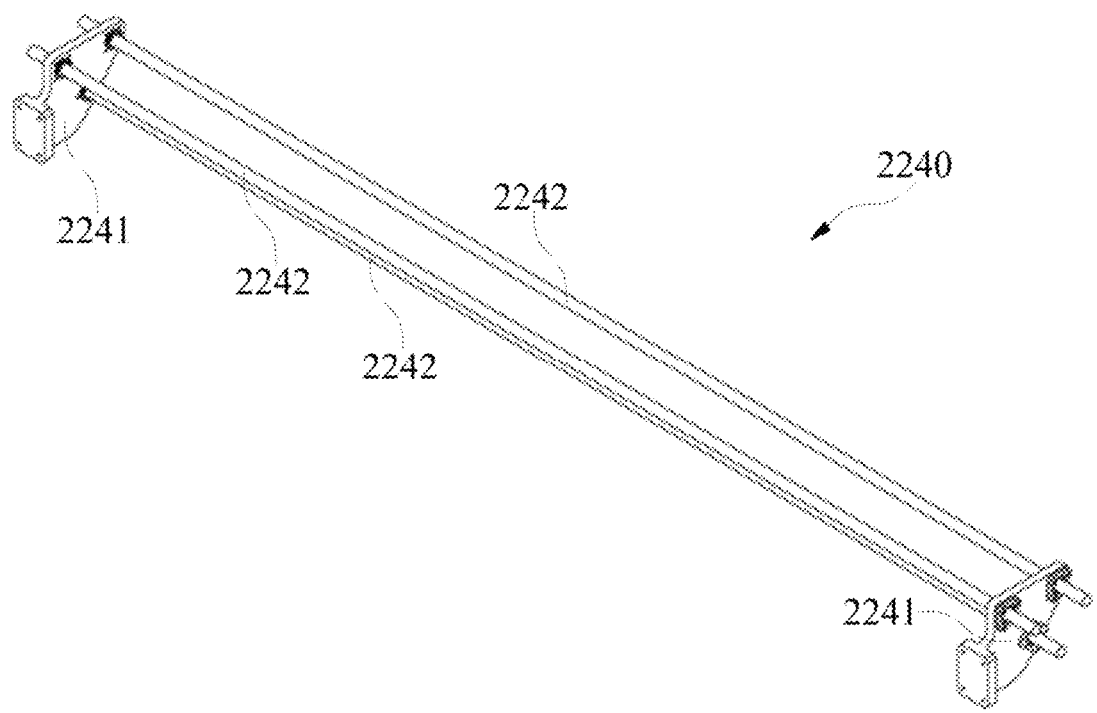
FIG. 12 is a schematic diagram of the structure of the second transmission unit for first adapter assembly according to an embodiment of the present disclosure.
Figure 13:
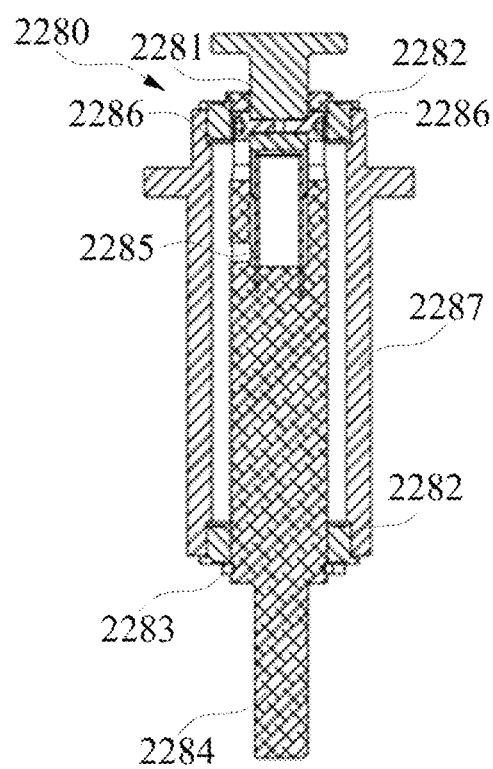
FIG. 13 is a schematic diagram of the structure of the long shaft output assembly for first adapter assembly according to an embodiment of the present disclosure.
Figure 14:
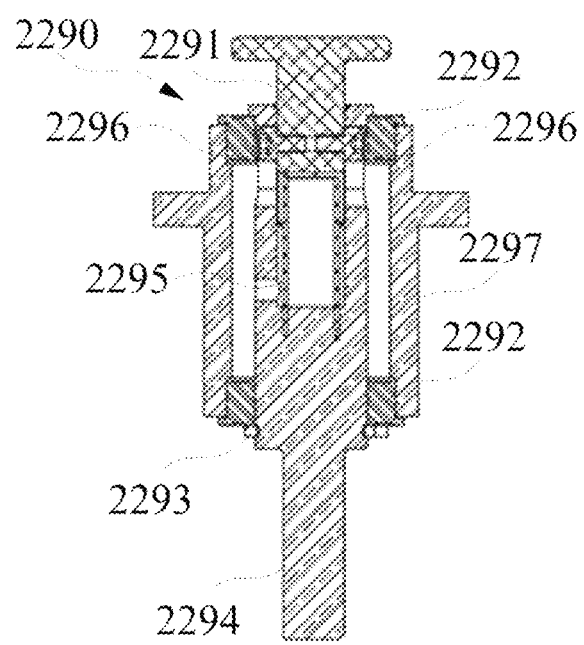
FIG. 14 is a schematic diagram of the structure of the short shaft output assembly for first adapter assembly according to an embodiment of the present disclosure.
Figure 15:
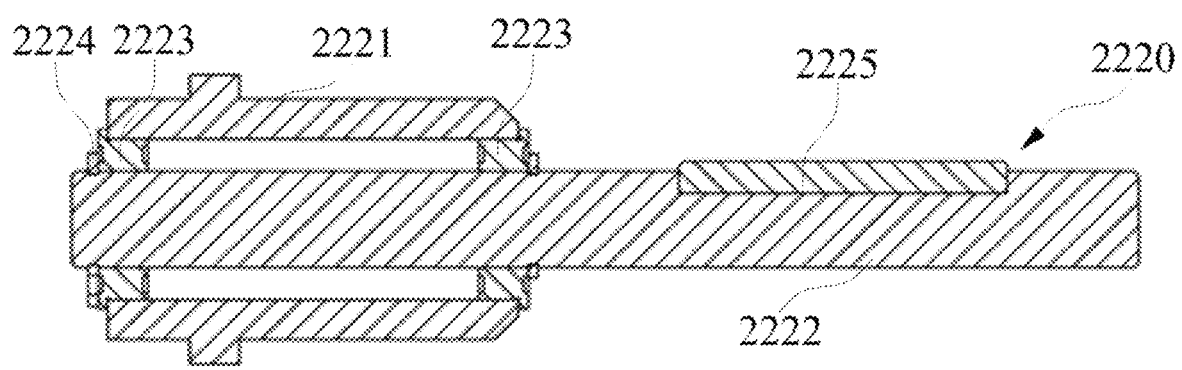
FIG. 15 is a schematic diagram of the structure of the axial end assembly for first adapter assembly according to an embodiment of the present disclosure.
Figure 16:
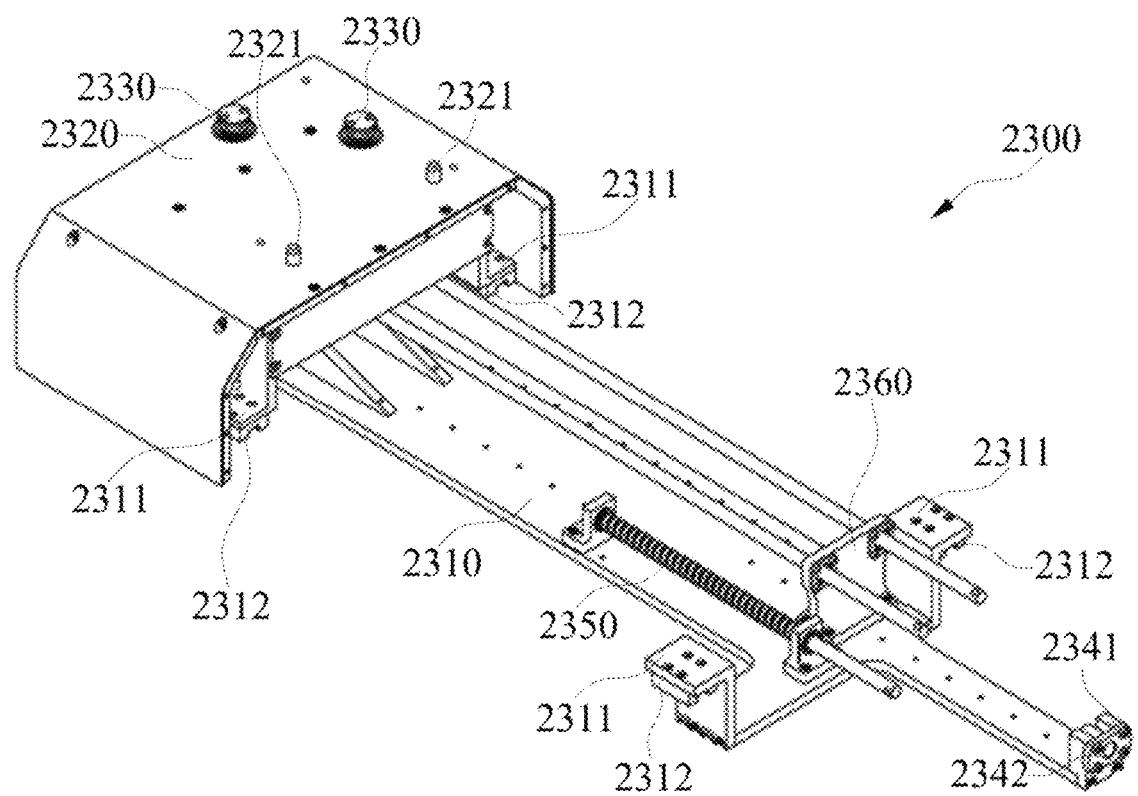
FIG. 16 is a schematic diagram of the structure of the second adapter transmission assembly according to an embodiment of the present disclosure, viewed from the first perspective.
Figure 17:
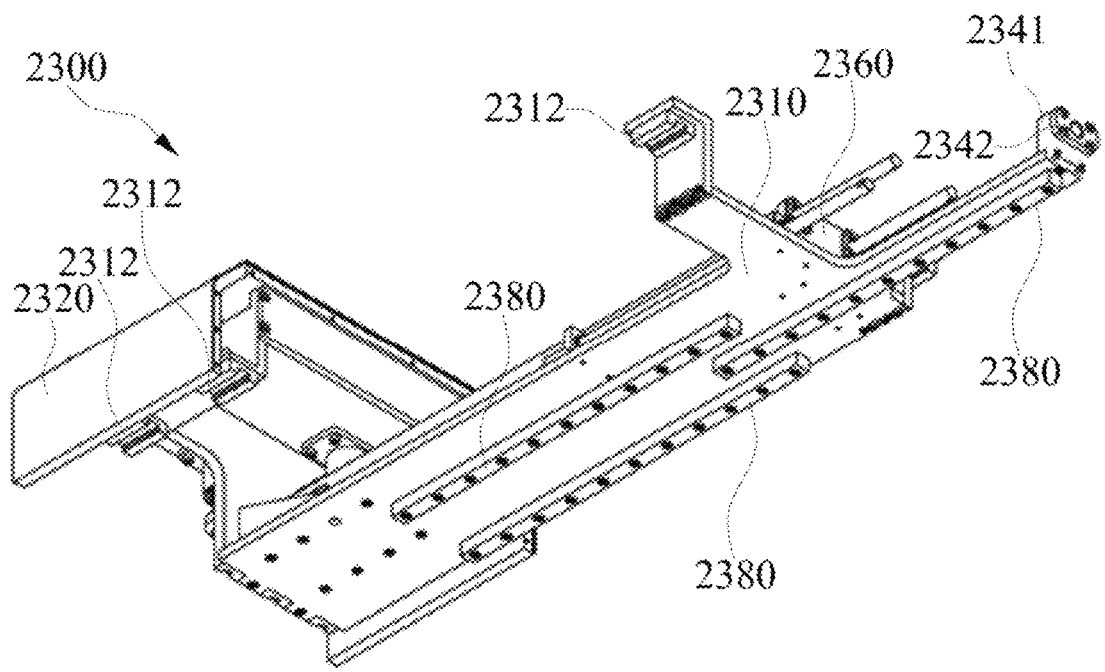
FIG. 17 is a schematic diagram of the structure of the second adapter transmission assembly according to an embodiment of the present disclosure, viewed from the second perspective.
Figure 18:
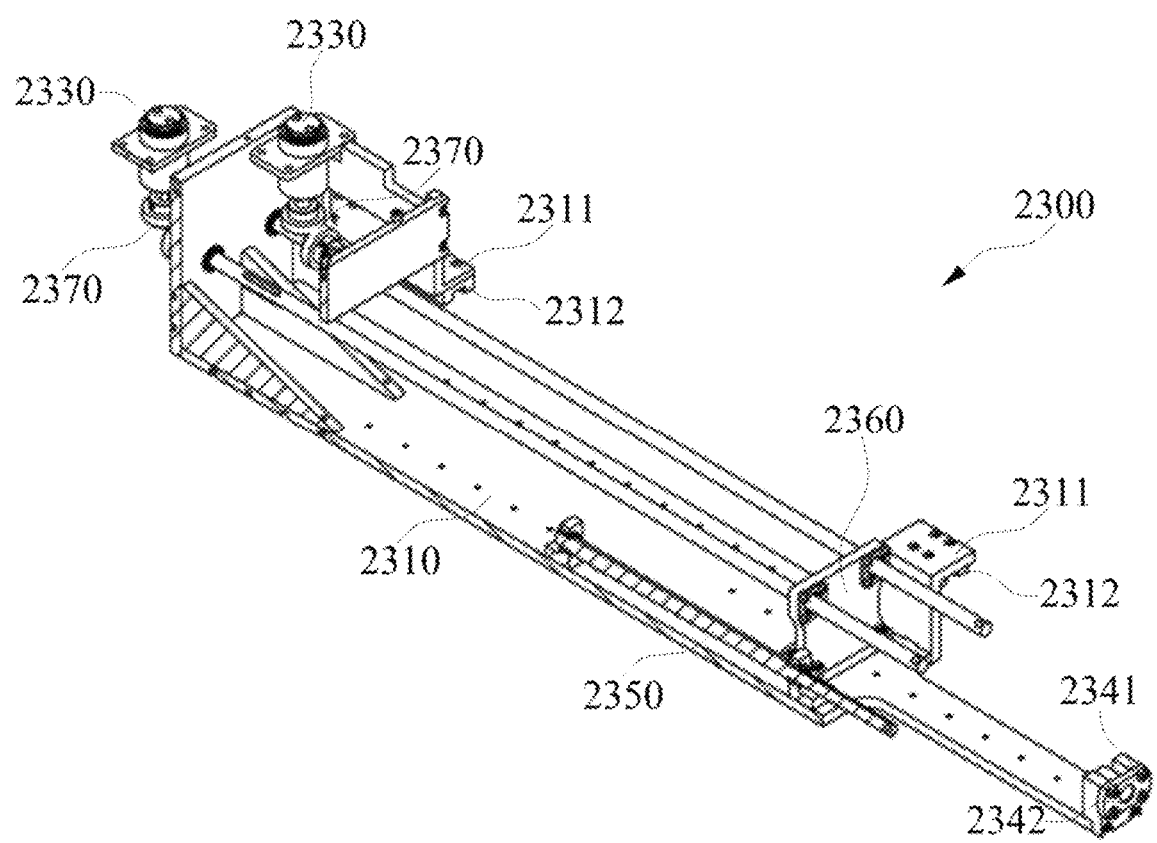
FIG. 18 is a schematic diagram of the cross-sectional structure of the second adapter transmission assembly according to an embodiment of the present disclosure.
Figure 19:
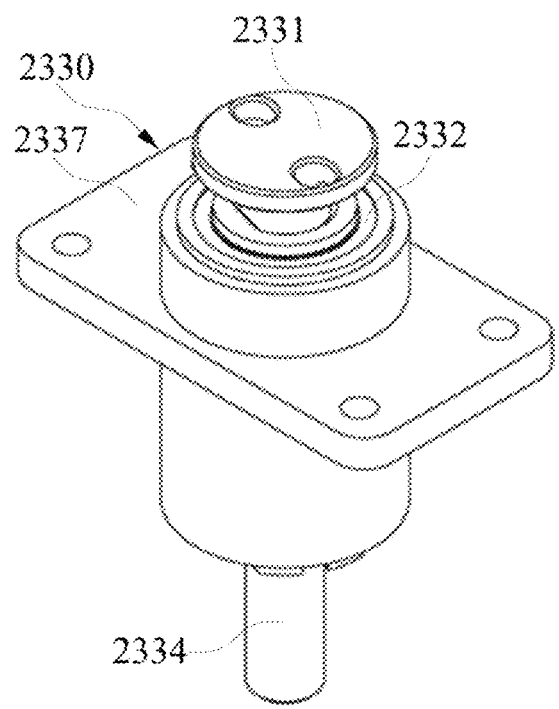
FIG. 19 is a schematic diagram of the structure of the second adapter output assembly according to an embodiment of the present disclosure.
Figure 20:
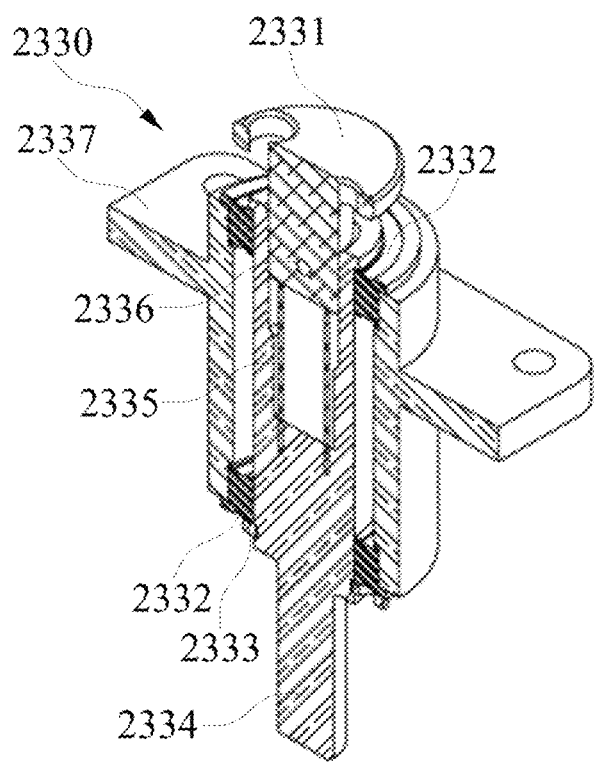
FIG. 20 is a schematic diagram of the cross-sectional structure of the second adapter output assembly according to an embodiment of the present disclosure.
Figure 21:
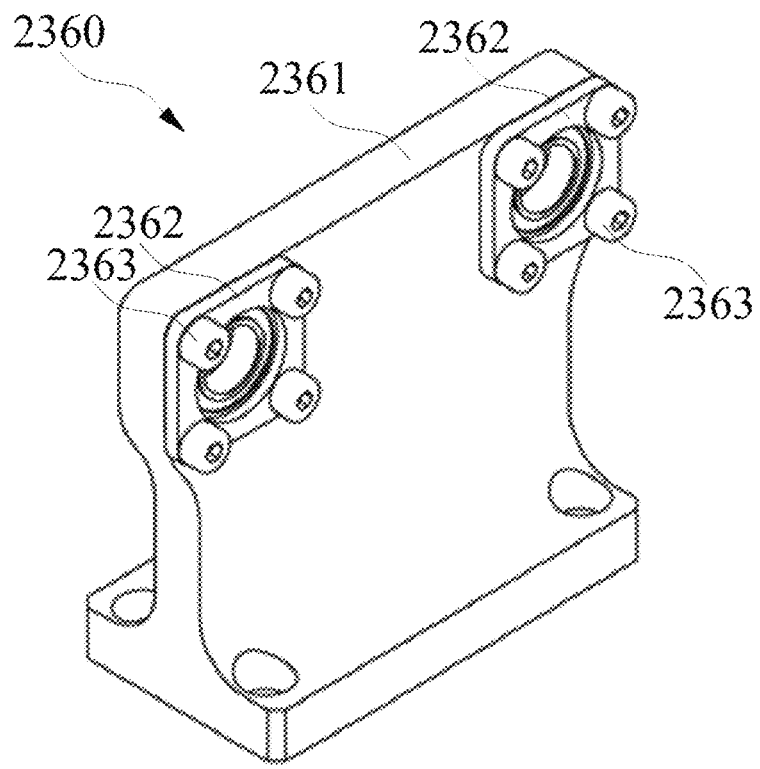
FIG. 21 is a schematic diagram of the structure of the dual bearing seat assembly according to an embodiment of the present disclosure.
Figure 22:
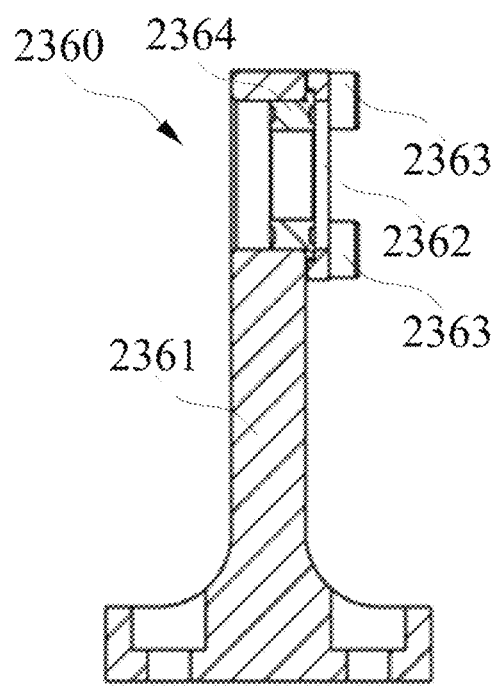
FIG. 22 is a cross-sectional view of the dual bearing seat assembly according to an embodiment of the present disclosure.
Figure 23:
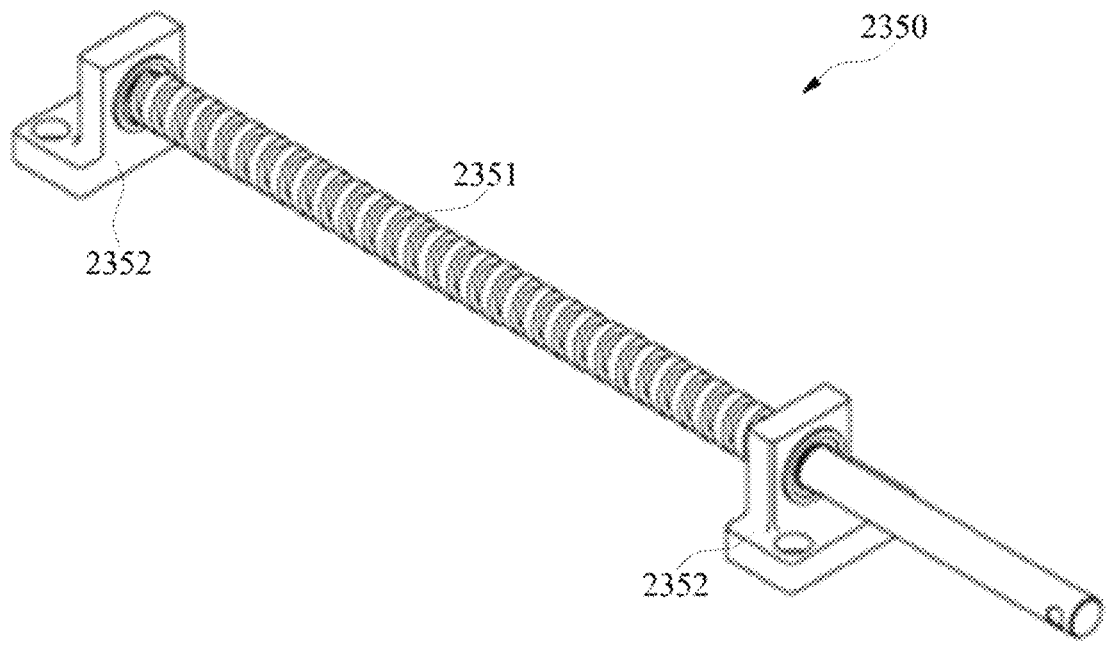
FIG. 23 is a schematic diagram of the structure of the trapezoidal screw unit according to an embodiment of the present disclosure.
Figure 24:
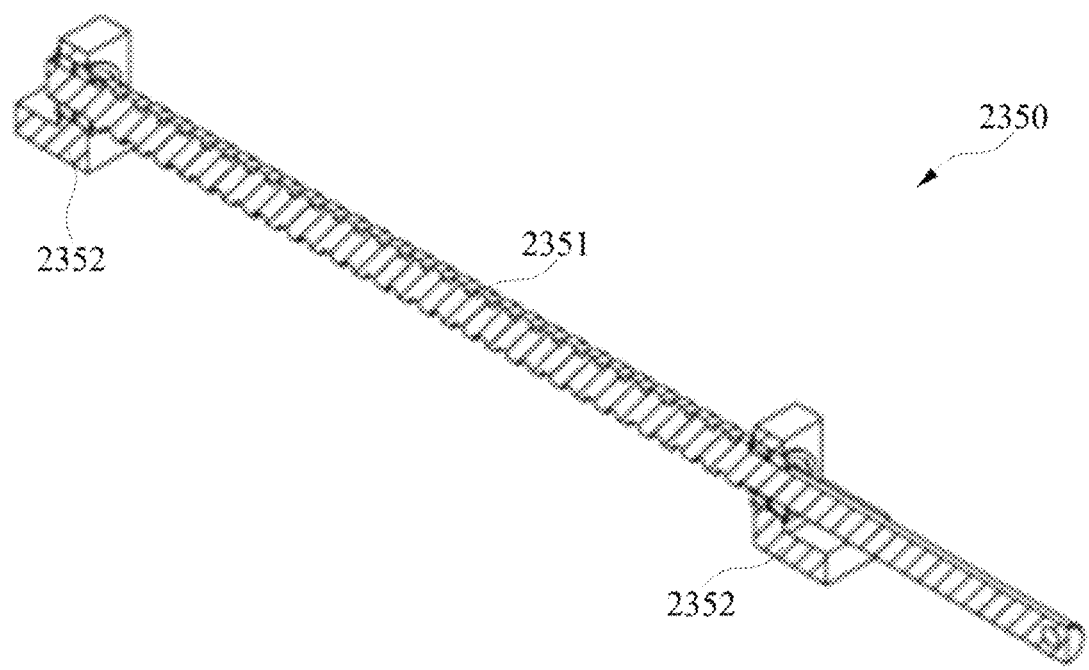
FIG. 24 is a cross-sectional view of the structure of the trapezoidal screw unit according to an embodiment of the present disclosure.
Figure 25:
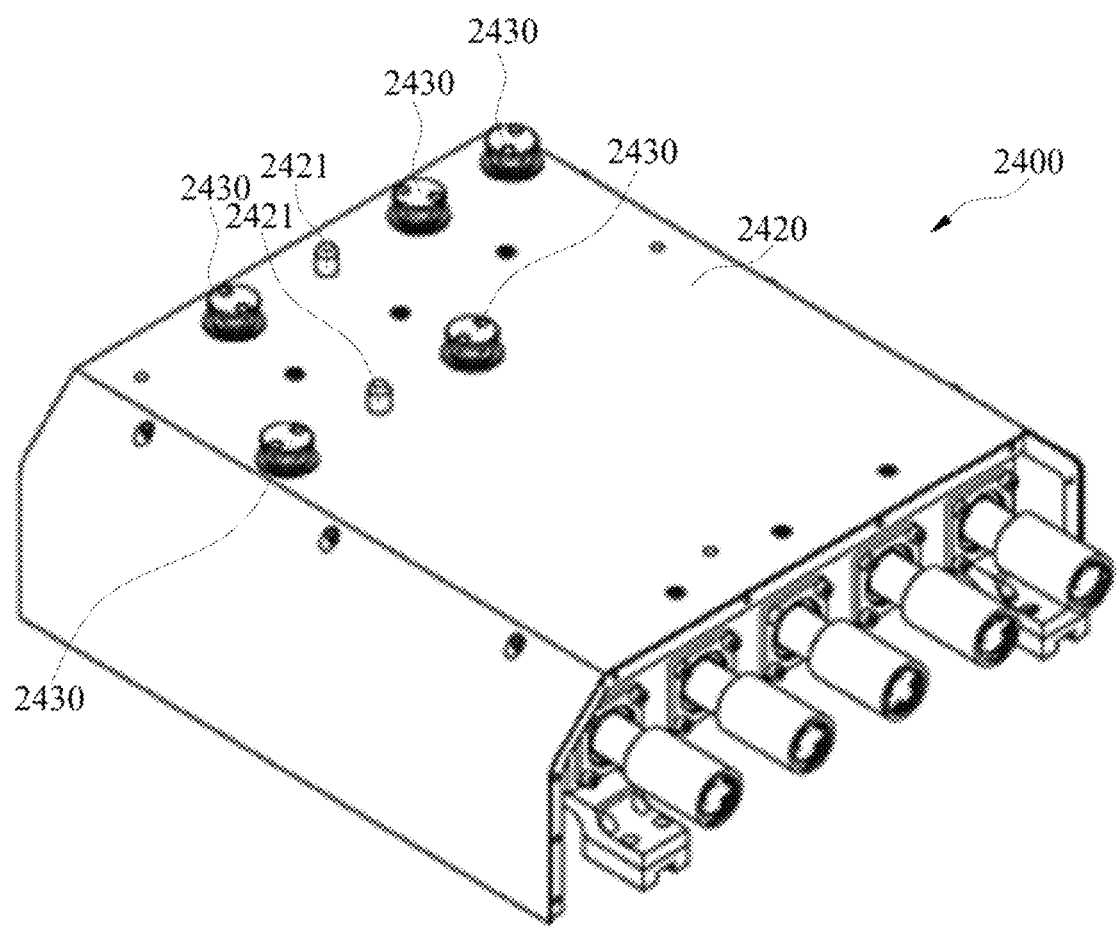
FIG. 25 is a schematic diagram of the structure of the third adapter transmission assembly according to an embodiment of the present disclosure.
Figure 26:
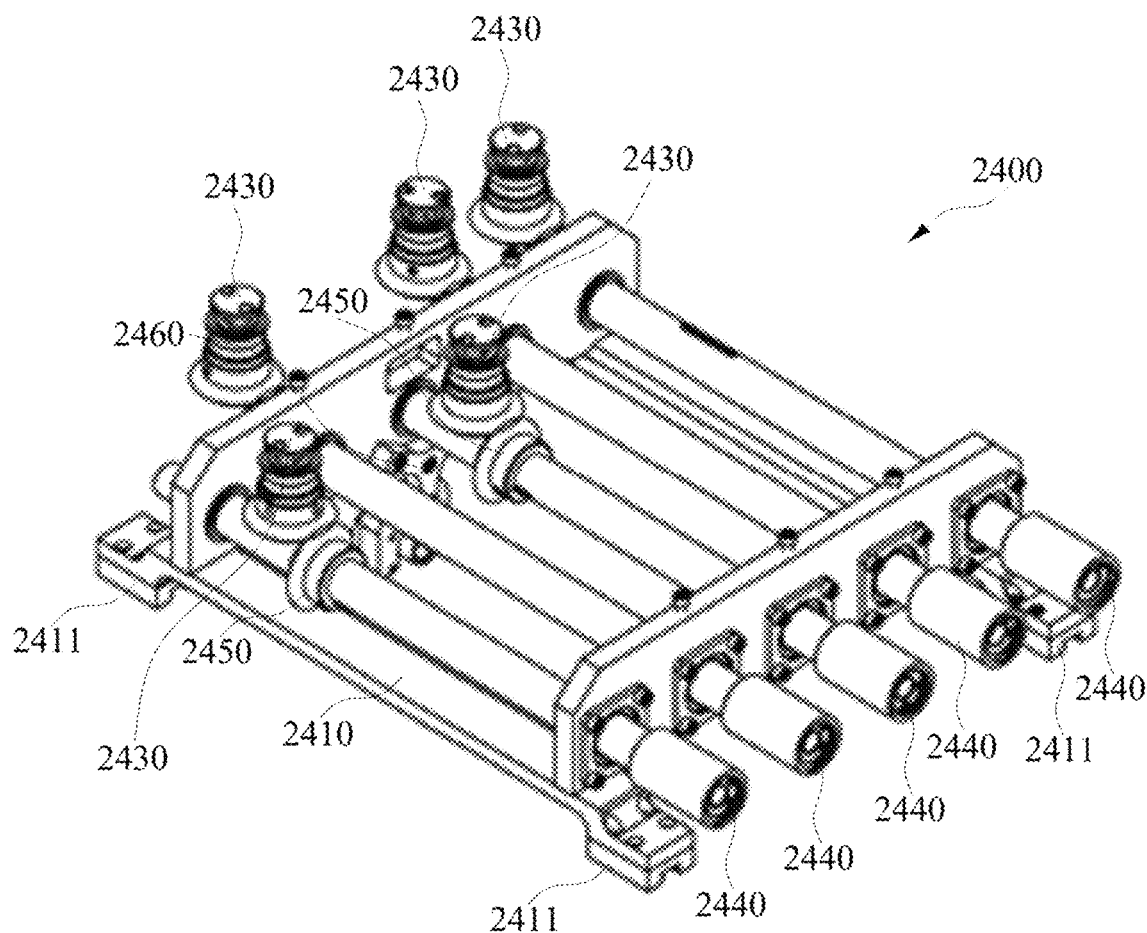
FIG. 26 is a schematic diagram of the structure of the third adapter transmission assembly according to an embodiment of the present disclosure excluding the third adapter mounting cover.
Figure 27:
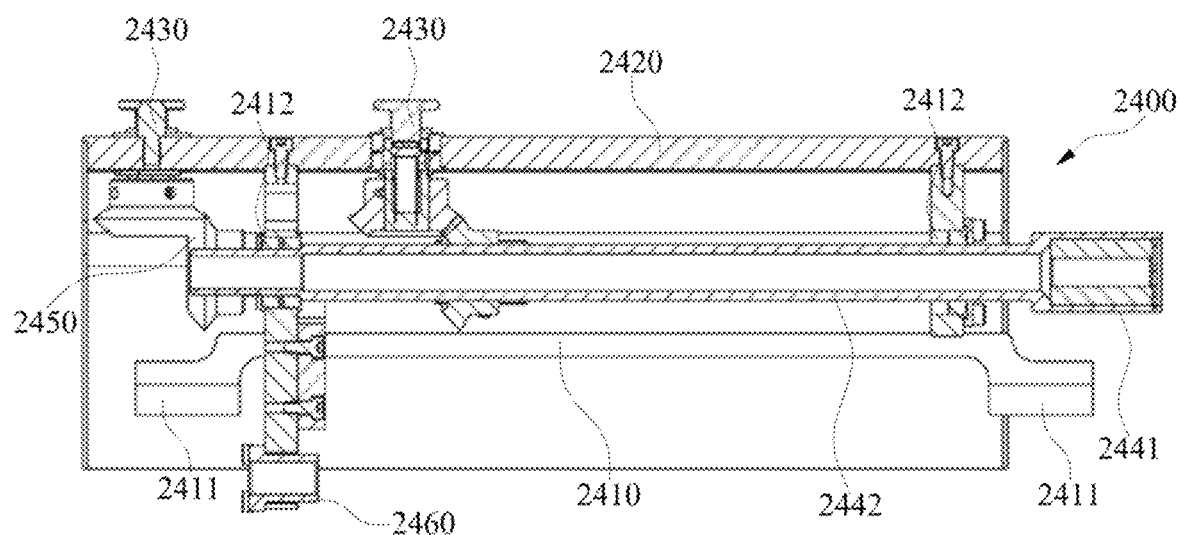
FIG. 27 is a cross-sectional view of the third adapter transmission assembly according to an embodiment of the present disclosure.
Figure 28:
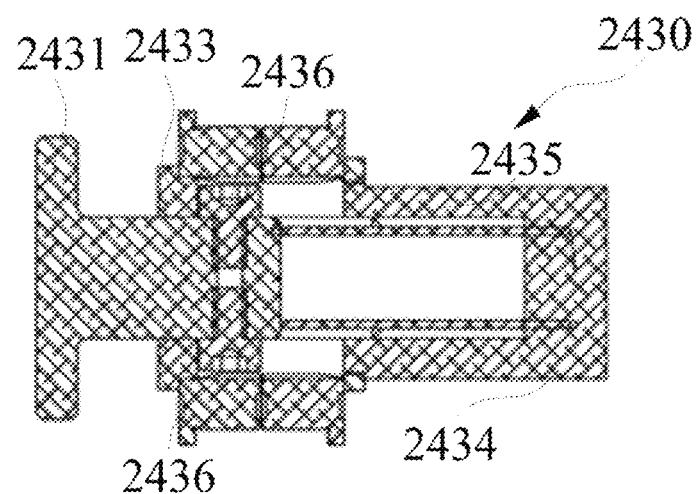
FIG. 28 is a cross-sectional view of the third adapter output assembly according to an embodiment of the present disclosure.
Figure 29:
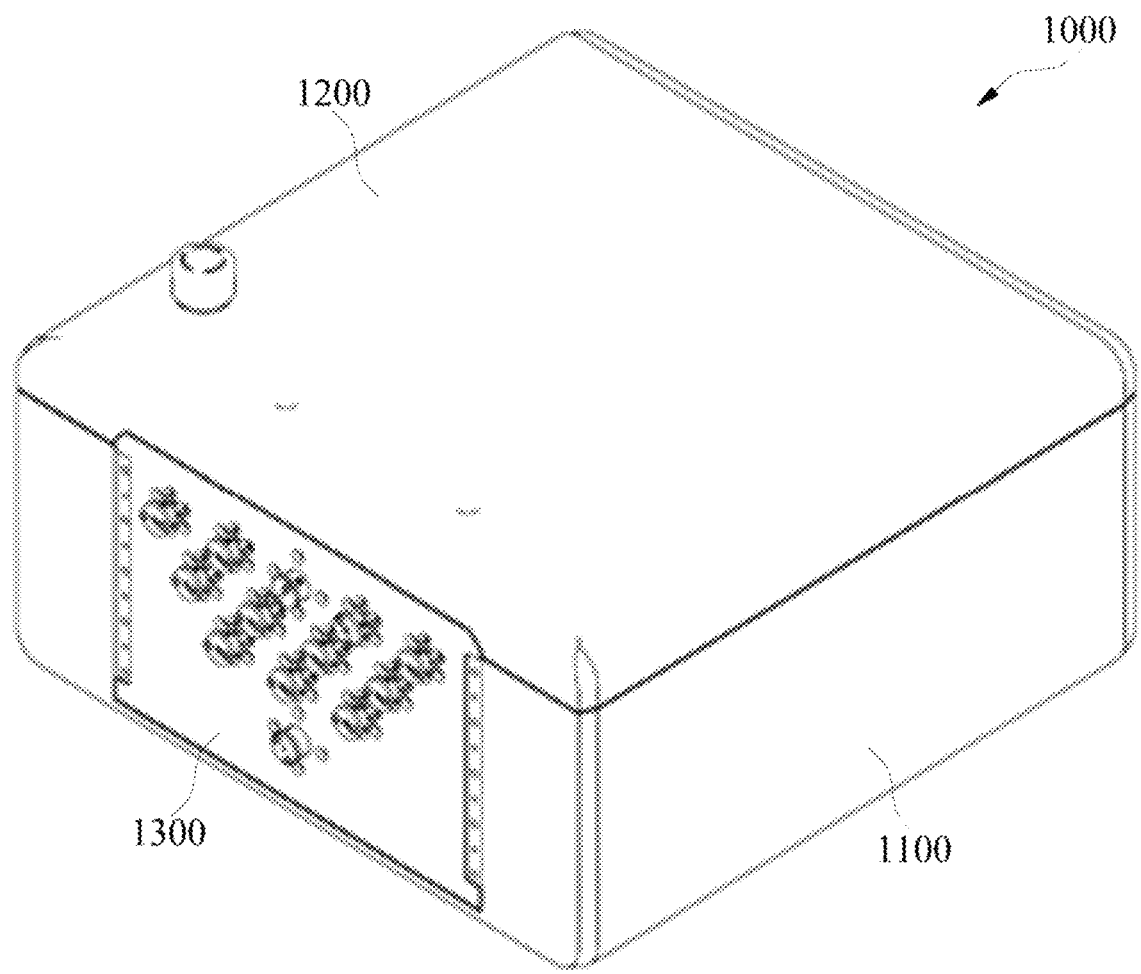
FIG. 29 is a schematic diagram of the structure of the power cabin according to an embodiment of the present disclosure.
Figure 30:
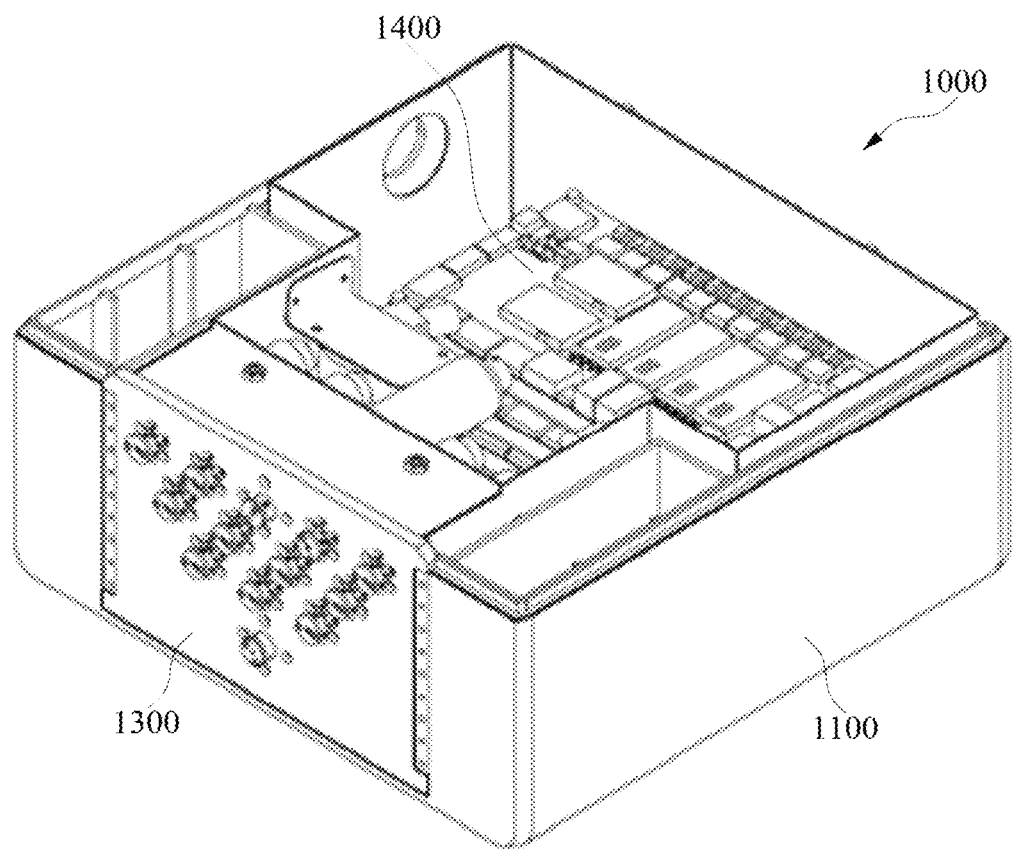
FIG. 30 is a schematic diagram of the structure of the power cabin according to an embodiment of the present disclosure excluding the top cover.
Figure 31:
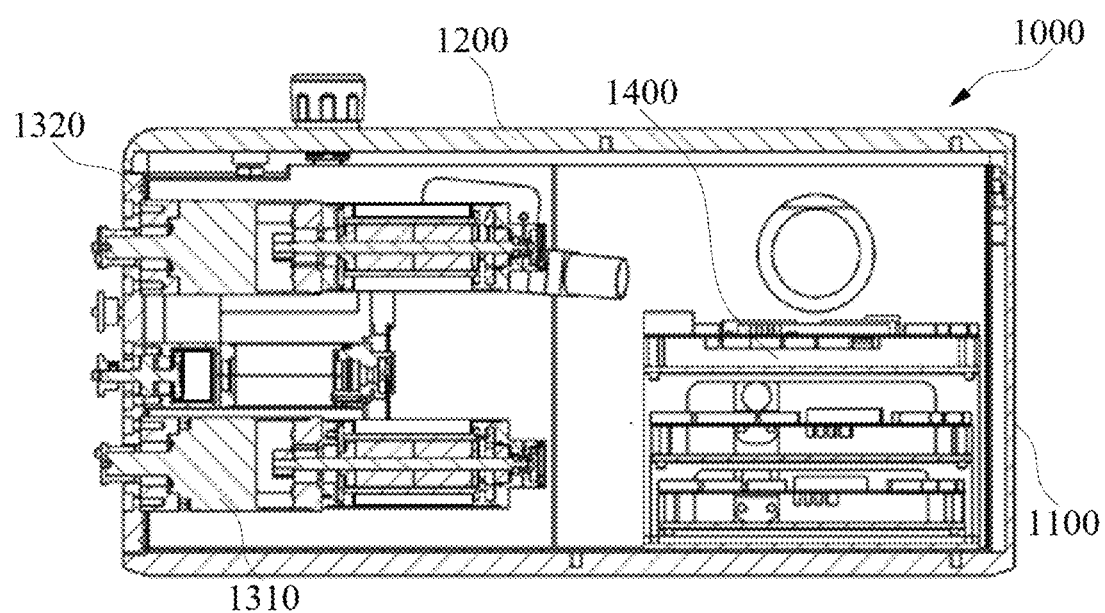
FIG. 31 is a cross-sectional view of the power cabin according to an embodiment of the present disclosure.
Figure 32:
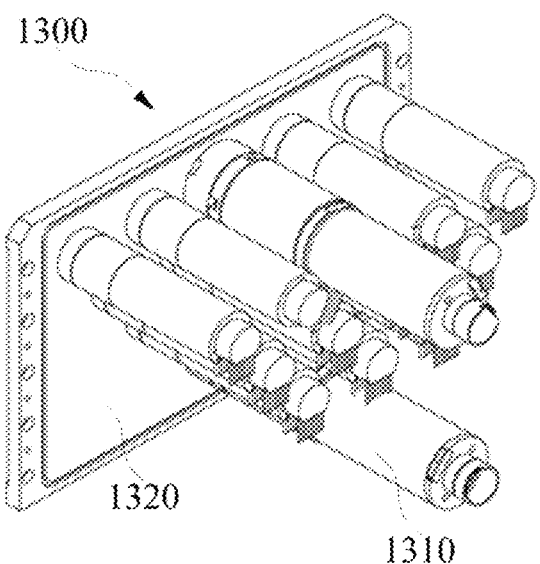
FIG. 32 is a schematic diagram of the structure of the assembly frame plate according to an embodiment of the present disclosure.
Figure 33:
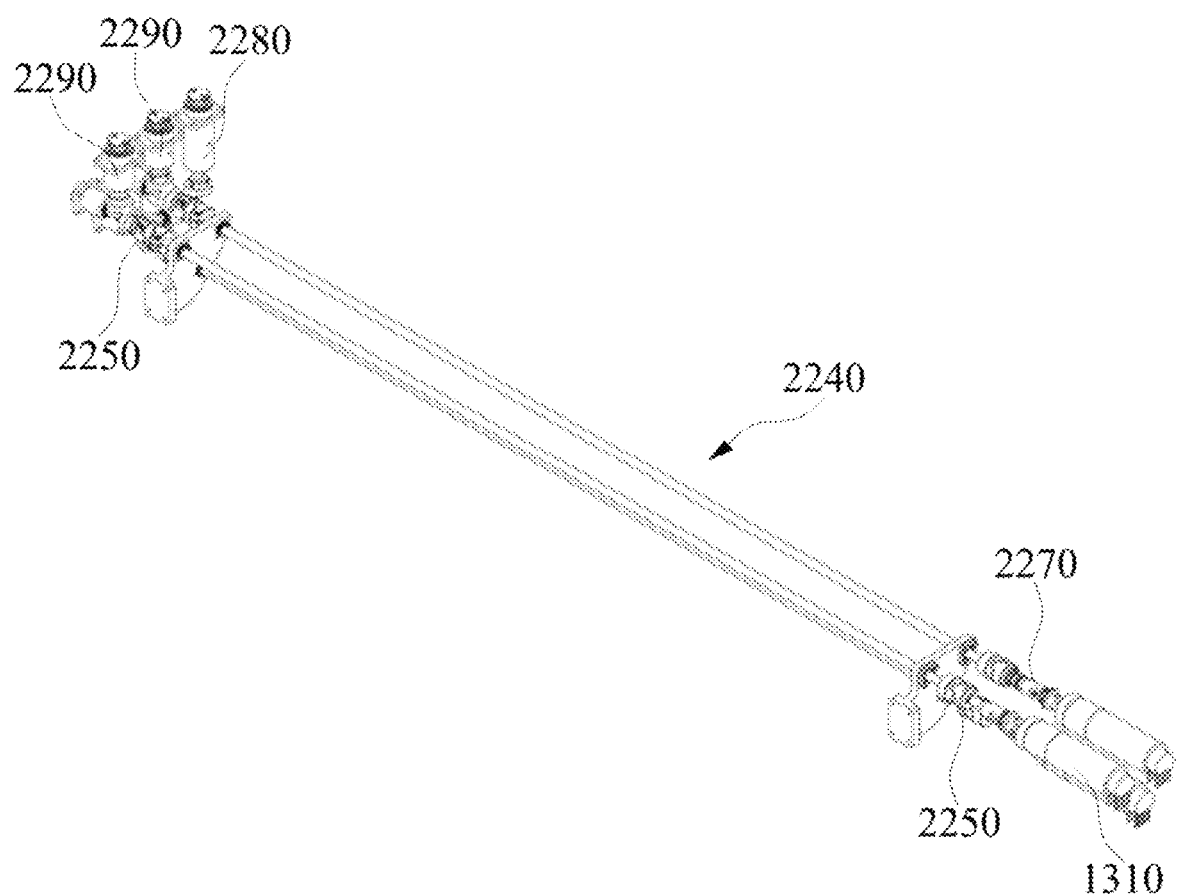
FIG. 33 is a schematic diagram of the structure of the first transmission module and the drive motors according to an embodiment of the present disclosure.
Figure 34:
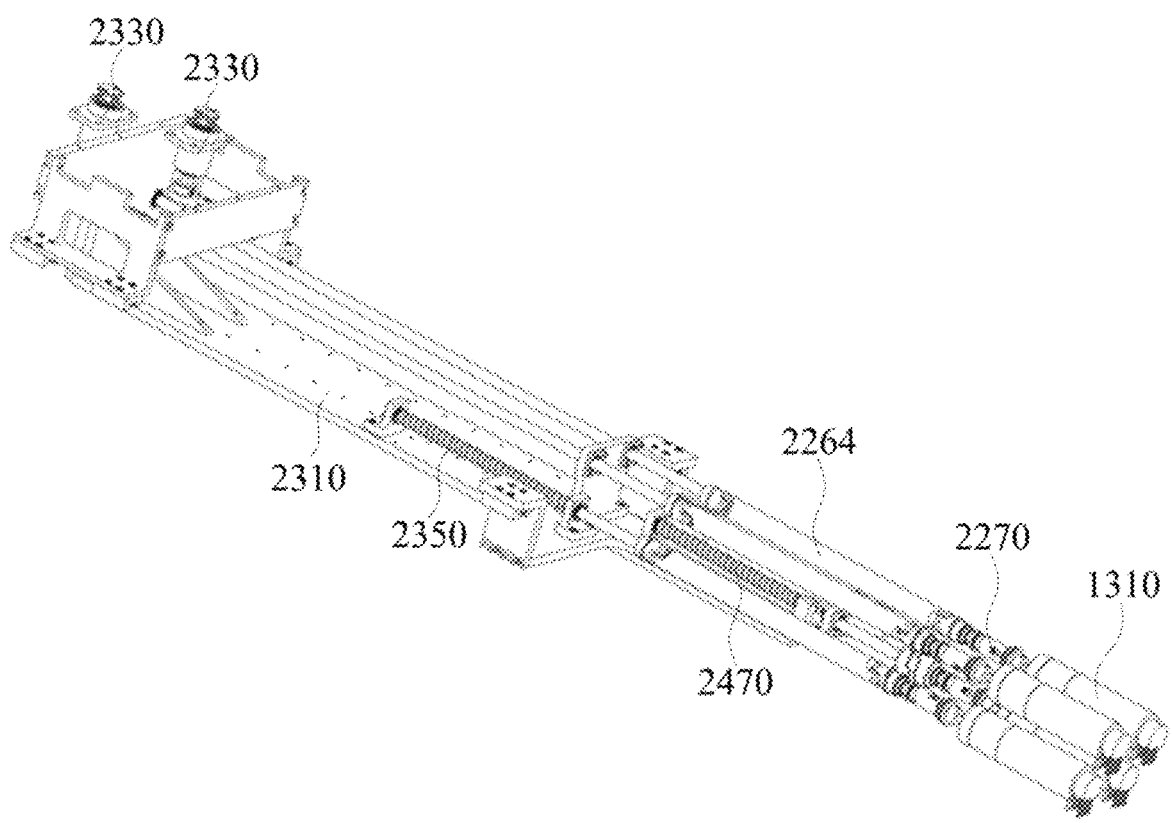
FIG. 34 is a schematic diagram of the structure of the valve repair system according to an embodiment of the present disclosure.
Figure 35:
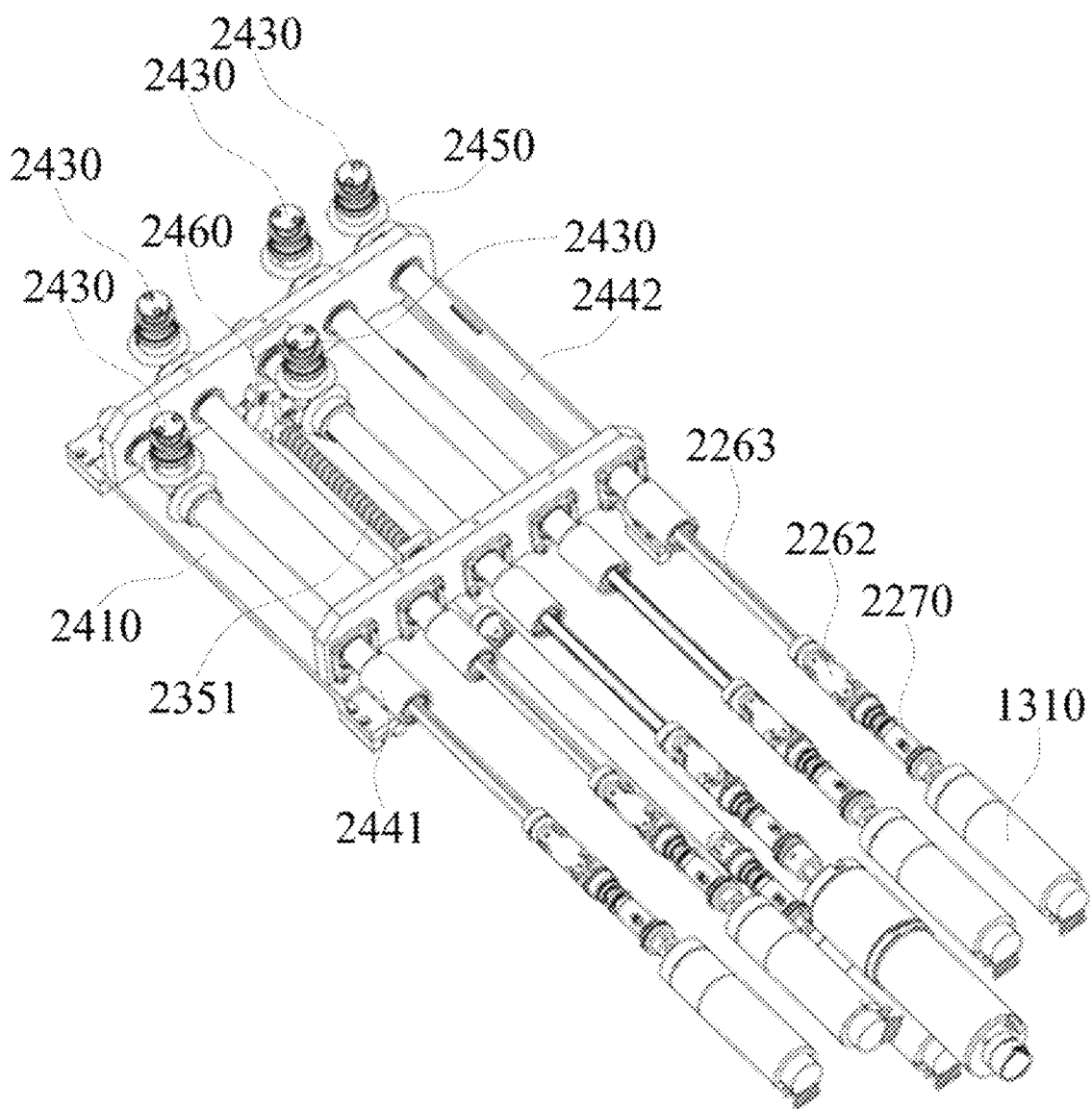
FIG. 35 is a schematic diagram of the structure of the mitral valve repair instrument according to an embodiment of the present disclosure.
Figure 36:
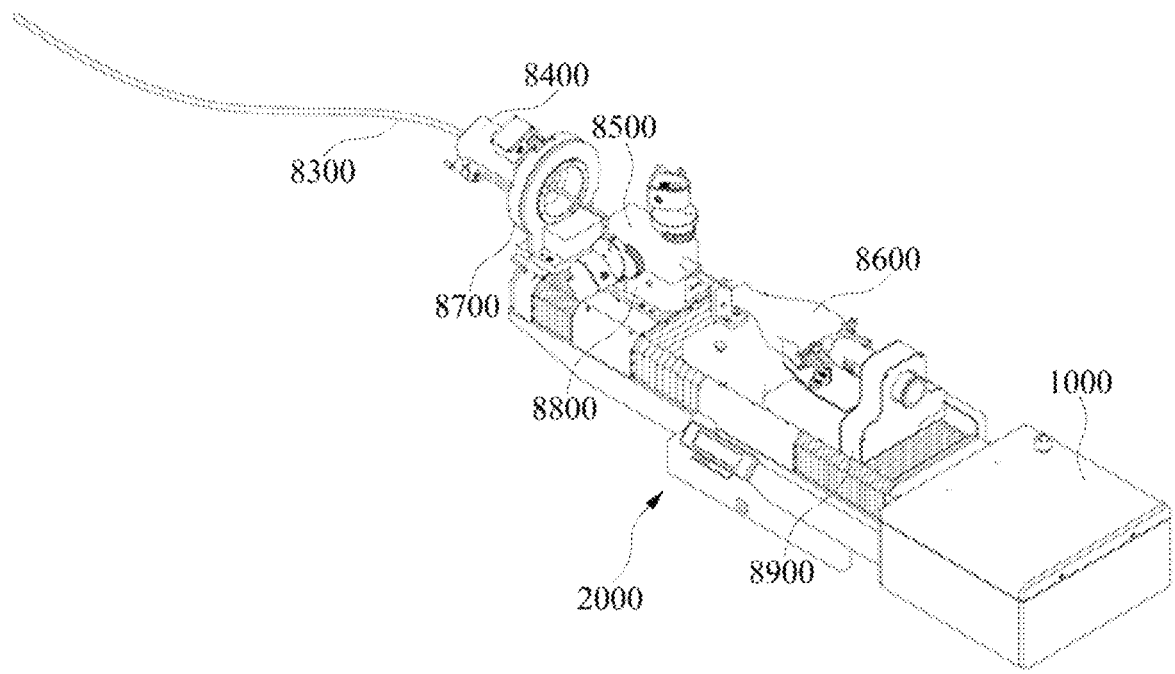
FIG. 36 is a schematic diagram of the structure of the second transmission module and the drive motors according to an embodiment of the present disclosure.
Figure 37:
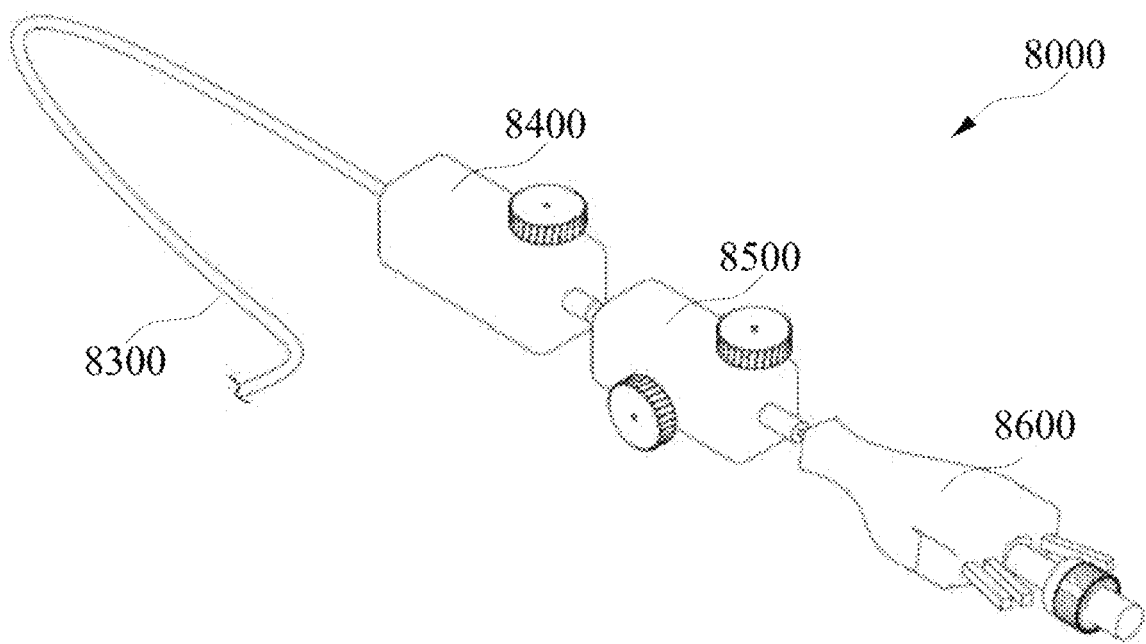
FIG. 37 is a schematic diagram of the structure of the third transmission module and the drive motors according to an embodiment of the present disclosure.
Figure 38:
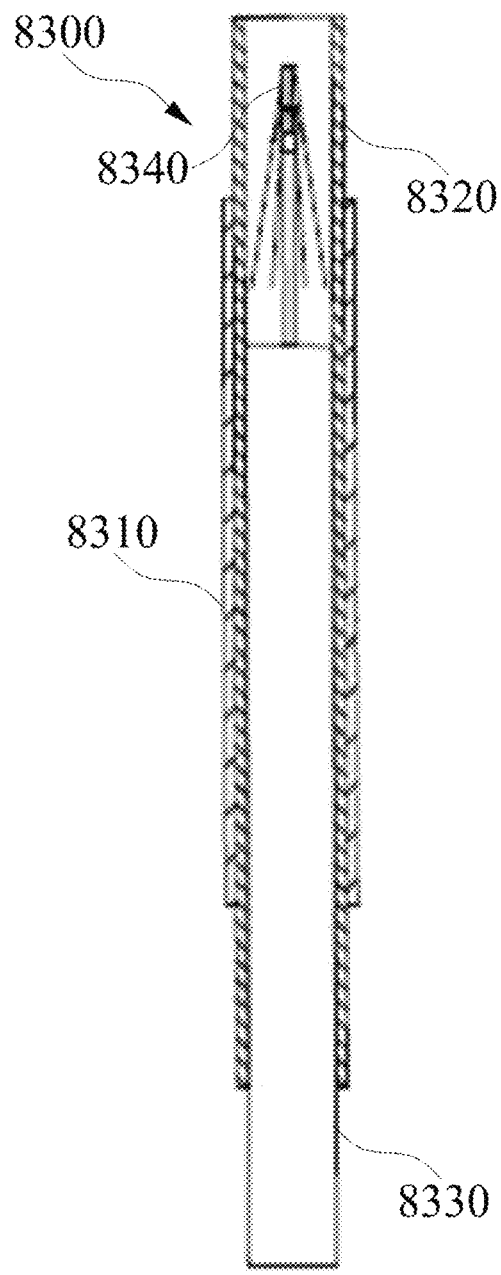
FIG. 38 is a cross-sectional view of the catheter assembly in the first state according to an embodiment of the present disclosure.
Figure 39:
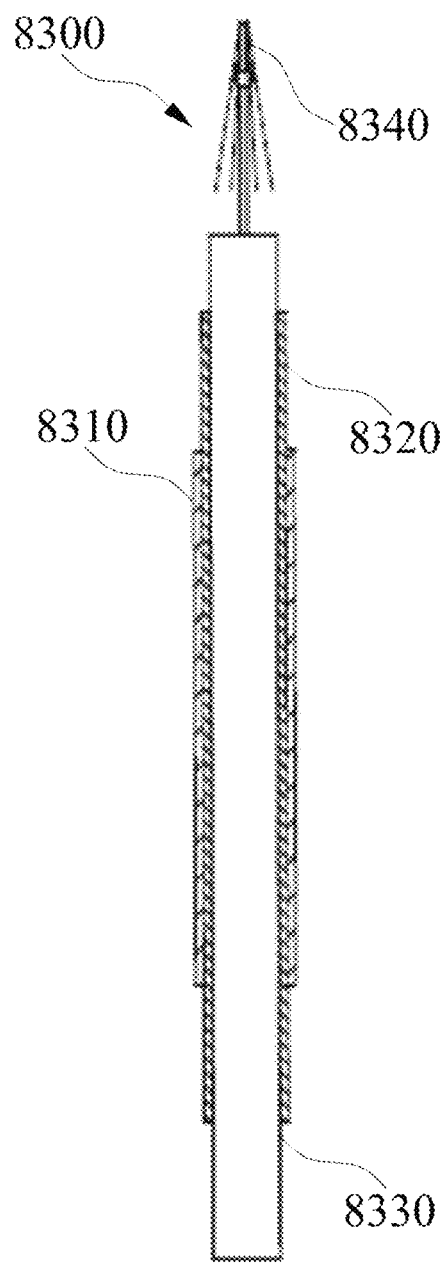
FIG. 39 is a cross-sectional view of the catheter assembly in the second state according to an embodiment of the present disclosure.
Figure 40:
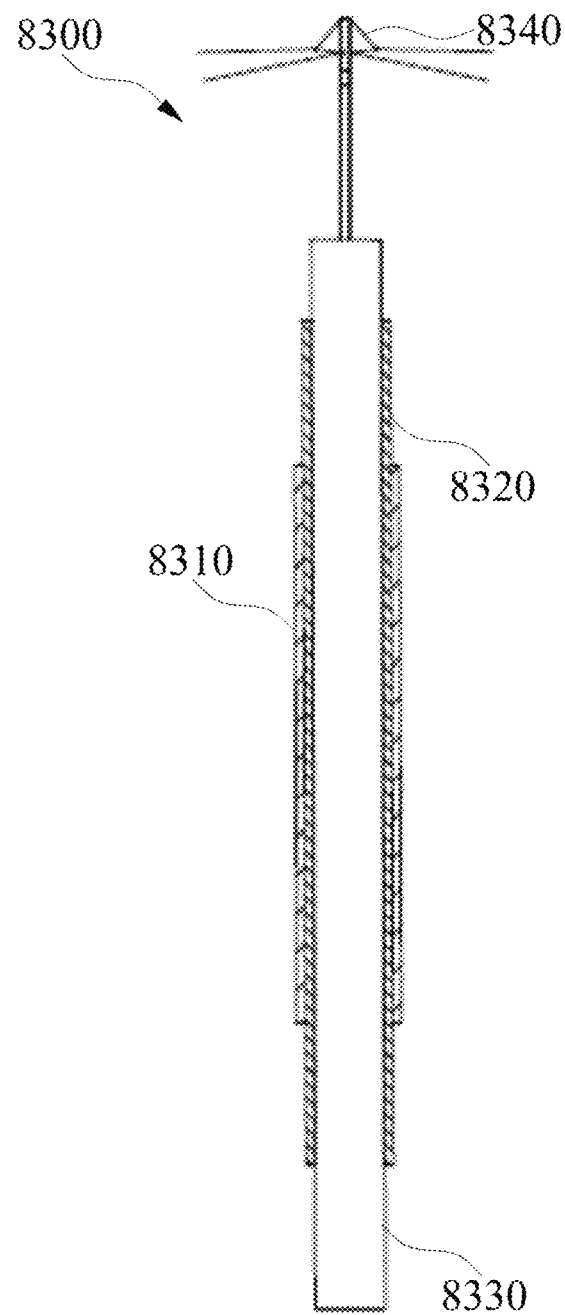
FIG. 40 is a cross-sectional view of the catheter assembly in the third state according to an embodiment of the present disclosure.

As shown in FIGS. 1 to 40, the present embodiments provide a surgical assistance device, including a robotic arm, a first adapter assembly 8700, a second adapter assembly, a third adapter assembly and a surgical execution apparatus, where the surgical execution apparatus is connected to the robotic arm, the first adapter assembly 8700, the second adapter assembly and the third adapter assembly. The surgical assistance device can be connected to the valve repair instrument through adapters to drive the movements of the instrument, thereby assisting surgeons in operating the valve repair instrument and complete the valve repair surgery.

The present embodiments are described by taking the mitral valve repair instrument 8000 as an example. The mitral valve repair instrument 8000 includes an implant and a delivery device. The delivery device includes a catheter assembly 8300, a first drive handle 8400, a second drive handle 8500, and a third drive handle 8600. The catheter assembly 8300 includes an outer catheter 8310, a middle catheter 8320 and an inner catheter 8330, which are nested together from the outside in. The inner catheter 8330 has two ends, i.e., a working end and an output end, where the working end is equipped with an implant, which in the present embodiments is a clip 8340 that can switch between an unfolded state and a folded state. The clip 8340 in the folded state can be stored in the middle catheter 8320. The clip 8340 has a clamping portion, which in the unfolded state of the clip 8340 forms a clamping space for holding the valve leaflet.

The surgical execution apparatus includes a transmission cabin 2000 and a power cabin 1000. The transmission cabin 2000 including a chassis assembly 2100 and a first adapter transmission assembly 2200, a second adapter transmission assembly 2300 and a third adapter transmission assembly 2400 that are movable relative to the chassis assembly 2100, the first adapter transmission assembly 2200 having a first transmission module detachably connected to the first adapter assembly 8700, the second adapter transmission assembly 2300 having a second transmission module detachably connected to the second adapter assembly 8800, and the third adapter transmission assembly 2400 having a third transmission module detachably connected to the third drive module. The power cabin 1000 is in transmission connection to the transmission cabin 2000, and configured to drive the first adapter assembly 8700 via the first transmission module, drive the second adapter assembly 8800 via the second transmission module, and drive the third adapter assembly 8900 via the third transmission module.

The surgical execution apparatus individually drives the first adapter assembly 8700, the second adapter assembly 8800, and the third adapter assembly 8900, which can enhance the flexibility of their output motions, facilitating refined operations required for surgical techniques, thus ensuring more precise, stable and safe operations of the surgical execution apparatus. Through the split design of the transmission cabin 2000 for power transmission and the power cabin 1000 for power generation, the active components are separated from the passive components in the surgical execution apparatus, thereby not only eliminating the risk of cable breakage or wear during transmission and movement of the surgical execution apparatus and avoiding issues related to the loosening of active connectors due to prolonged use, but also improving the electromagnetic shielding performance by isolating the active components within the power cabin 1000. The transmission structure of the transmission cabin 2000 is simple and compact, which can effectively reduce the structural size of the surgical execution apparatus, and can improve the transmission efficiency, thus contributing to more stable, accurate and reliable operations. The apparatus with above structural design also offers high scalability, allowing for the replacement of different adapters according to specific surgical technique requirements, thereby expanding the range of applicable surgical techniques. The above improvements in the surgical execution apparatus can lower the experience required for surgeons in operating surgical instruments, decrease their physical exertion, and mitigate the impact of radiation from the surgical execution apparatus on them, while facilitating the intelligent operation of minimally invasive surgical diagnosis and treatment. The surgical execution apparatus, when being used by surgeons for surgical techniques, can ensure the stability and accuracy of surgical operations, and improve efficiency thereof, thus shortening the procedure durations. The application of the surgical execution apparatus also contributes to improving the working environment for surgeons, reducing the physical demands on them, and shortening the learning curves required for them to master complex surgical techniques.

In the present embodiments, the first adapter transmission assembly 2200 is slidably attached to the chassis assembly 2100 to slide along an adjustment direction that is parallel to a lengthwise direction of the transmission cabin 2000, the second adapter transmission assembly 2300 is slidably attached to the first adapter transmission assembly 2200 to slide along the adjustment direction, and the third adapter transmission assembly 2400 is slidably attached to the second adapter transmission assembly 2300 to slide along the adjustment direction.

The above structural layout enables the first adapter transmission assembly 2200, the second adapter transmission assembly 2300 and the third adapter transmission assembly 2400 movable relative to the chassis assembly 2100. This layout is simple and reliable, achieving a rational arrangement of the transmission cabin 2000, thereby reducing the space occupied by the transmission cabin 2000, and decreasing the difficulty of adjusting positions of the first adapter transmission assembly 2200, the second adapter transmission assembly 2300 and the third adapter transmission assembly 2400, and minimizing the likelihood of positional conflicts among the components within the transmission cabin 2000.

Furthermore, the power cabin 1000 includes a motor assembly 1300, which includes an assembly frame plate 1320 and a plurality of drive motors 1310 mounted on the assembly frame plate 1320, where output ends of the drive motors 1310 extend through the assembly frame plate 1320; the transmission cabin 2000 includes an axial end fixing assembly 2260 provided at one end of the first adapter transmission assembly 2200, the axial end fixing assembly 2260 including a fixing end plate 2261 and input end connection assemblies 2270 extending through and rotatably connected to the fixing end plate 2261; the input end connection assemblies 2270 and the drive motors 1310 are equal in number, and each input end connection assembly 2270 is coaxially and detachably connected to an output end of one drive motor 1310.

The design of matching the input end connection assemblies 2270 with the output ends of the drive motors 1310 enables smooth transmission between the power cabin 1000 and the transmission cabin 2000, and achieves modular designs for both the power cabin 1000 and the transmission cabin 2000, thereby enhancing the flexibility of the use of the surgical execution apparatus, thus facilitating the expansion of its range of applicable surgical techniques.

In the present embodiments, the power cabin 1000 is installed on the right side of the transmission cabin 2000. The chassis assembly 2100 is located at the bottom of the transmission cabin 2000, the first adapter transmission assembly 2200 is installed above the chassis assembly 2100, the second adapter transmission assembly 2300 is installed above the first adapter transmission assembly 2200, the third adapter transmission assembly 2400 is installed on the right side of the second adapter transmission assembly 2300, and the axial end fixing assembly 2260 is provided on the right side of the transmission cabin 2000. The axial end fixing assembly 2260 can be quickly coupled to the motor assembly 1300, allowing for rapid attachment and detachment of the transmission cabin 2000 to and from the power cabin 1000.

The transmission cabin 2000 further includes a first bellows cover 2910, a second bellows cover 2920, and a third bellows cover 2930, where the first bellows cover 2910 is fixedly connected to the first adapter transmission assembly 2200 on the left side and to the second adapter transmission assembly 2300 on the right side, the second bellows cover 2920 is fixedly connected to the second adapter transmission assembly 2300 on the left side and to the third adapter transmission assembly 2400 on the right side, and the third bellows cover 2930 is fixedly connected to the third adapter transmission assembly 2400 on the left side and to the first adapter transmission assembly 2200 on the right side. The first bellows cover 2910 is configured to provide sealing protection during relative linear motion between the first adapter transmission assembly 2200 and the second adapter transmission assembly 2300; the second bellows cover 2920 is configured to provide sealing protection during relative linear motion between the second adapter transmission assembly 2300 and the third adapter transmission assembly 2400; and the third bellows cover 2930 is configured to provide sealing protection during relative linear motion between the third adapter transmission assembly 2400 and the first adapter transmission assembly 2200.

Specifically, the power cabin 1000 further includes a bottom shell 1100 and a top cover 1200 buckled onto the top of the bottom shell 1100. The bottom shell 1100 and the top cover 1200 enclose a storage space with a driver assembly 1400 and all the drive motors 1310 being installed therein, where the driver assembly 1400 is communicatively connected to the motor assembly 1300.

Furthermore, the chassis assembly 2100 includes a bottom bracket 2110 and a guide rail connection plate 2130 slidably mounted thereon, and the first adapter transmission assembly 2200 includes a frame 2210, with the axial end fixing assembly 2260 being fixedly connected to one end of the frame 2210, where the guide rail connection plate 2130 is fixedly connected to the frame 2210. A first trapezoidal nut 2123 is installed on the bottom bracket 2110, and a first trapezoidal screw 2132 is rotatably connected to the guide rail connection plate 2130 to rotate around an adjustment direction, where the first trapezoidal nut 2123 is in transmission engagement with the first trapezoidal screw 2132; the second adapter transmission assembly 2300 includes a transmission support plate 2310 with a second trapezoidal nut 2342 being installed thereon, and a second trapezoidal screw 2470 is rotatably connected to the axial end fixing assembly 2260 to rotate around the adjustment direction, where the second trapezoidal nut 2342 is in transmission engagement with the second trapezoidal screw 2470; and a third trapezoidal screw 2351 is rotatably connected to the transmission support plate 2310 to rotate around the adjustment direction, and the third adapter transmission assembly 2400 includes a slider connection plate 2410 with a third trapezoidal nut 2460 installed thereon, where the third trapezoidal nut 2460 is in transmission engagement with the third trapezoidal screw 2351.

The above structural design of the transmission cabin 2000 establishes the transmission relationship between the chassis assembly 2100, the first adapter transmission assembly 2200, the second adapter transmission assembly 2300 and the third adapter transmission assembly 2400, so that the relative movements between the above components is enabled by driving the first trapezoidal screw 2132, the second trapezoidal screw 2470 and the third trapezoidal screw 2351, thus decreasing the difficulty of driving and ensuring stable, long-term operation of the transmission cabin 2000.

In the present embodiments, a chassis main beam 2120 is fixedly screwed to the bottom bracket 2110, with the guide rail connection plate 2130 being slidably provided on the chassis main beam 2120, where the first trapezoidal screw 2132 is fixed to the guide rail connection plate 2130 at both ends via respective first bearing seats 2131 (each having a bearing), and the first trapezoidal nut 2123 is installed on the first nut fixing seat 2122 which is in turn fixedly connected to the chassis main beam 2120. When the first trapezoidal nut 2123 rotates, since the first trapezoidal nut 2123 is installed on the chassis main beam 2120, the entire first trapezoidal screw 2132 can be driven to move axially. Considering that the first trapezoidal screw 2132 is installed on the guide rail connection plate 2130, the guide rail connection plate 2130 is in turn driven to slide axially. During the entire movement process, the first trapezoidal screw 2132 bears minimal radial load, with all radial loads being transferred to the chassis main beam 2120 via the slider engagement, allowing for reduced structural size of the chassis assembly 2100, thus achieving a more compact transmission structure of the chassis assembly 2100. Specifically, a pair of first linear guide rails 2121 extending along the adjustment direction is provided on the chassis main beam 2120, where the guide rail connection plate 2130 is slidably provided on the first linear guide rails 2121.

Furthermore, the first trapezoidal screw 2132 is coaxially fixed to one of the input end connection assemblies 2270 via a first cross slider coupling 2140 and one of second cross slider couplings 2265 in sequence; the second trapezoidal screw 2470 is coaxially fixed to one of the input end connection assemblies 2270 via one of the second cross slider couplings 2265; and the third trapezoidal screw 2351 is coaxially fixed to one of the input end connection assemblies 2270 via one of telescopic universal couplings 2264 and one of the second cross slider couplings 2265 in sequence.

The above design establishes the transmission connection between the axial end fixing assembly 2260 and the first trapezoidal screw 2132, the second trapezoidal screw 2470 and the third trapezoidal screw 2351, which simplifies the transmission mode between the transmission cabin 2000 and the power cabin 1000, and optimizes the specific structure of the transmission cabin 2000, thereby facilitating the smooth operation of the surgical execution apparatus.

For example, the other end of the frame 2210 is equipped with a first transmission unit for first adapter assembly 2230 including a first adapter assembly mounting plate 2231 fixed to the frame 2210, where a plurality of first positioning pins 2232 for pinning and positioning the first adapter assembly 8700 are provided on the first adapter assembly mounting plate 2231 to protrude therefrom; a second adapter mounting cover 2320 is provided above the transmission support plate 2310, where a plurality of second positioning pins 2321 for pinning and positioning the second adapter assembly 8800 are provided on the second adapter mounting cover 2320 to protrude from; and a third adapter mounting cover 2420 is provided above the slider connection plate 2410, where a plurality of third positioning pins 2421 for pinning and positioning the third adapter assembly 8900 are provided on the third adapter mounting cover 2420 to protrude therefrom.

Specifically, a second linear guide rail 2212 extending along the adjustment direction is provided on the top end of the frame 2210, and a slider fixing plate 2311 is further fixed to the transmission support plate 2310, with a first slider 2312 being fixed to the bottom of the slider fixing plate 2311, where the first slider 2312 is slidably engaged with the second linear guide rail 2212.

In the present embodiments, the drive motor 1310 drives the second trapezoidal screw 2470 to rotate. Since the second trapezoidal nut 2342 is fixed in its circumferential direction, the second trapezoidal nut 2342 can drive the second adapter transmission assembly 2300 to translate. During this process, the telescopic universal coupling 2264 extends or retracts, thus enabling the horizontal movement under the constraint of the sliding connection. The drive motor 1310 drives the third trapezoidal screw 2351 to rotate. Since the third trapezoidal nut 2460 is fixed in its circumferential direction, the third trapezoidal nut 2460 can drive the third adapter transmission assembly 2400 to translate. During this process, the ball spline body 2441 and the ball spline inner shaft 2263 form a translational friction pair, thus enabling the horizontal movement under the constraint of the sliding connection. Specifically, the second trapezoidal nut 2342 is rotatably connected to the second nut fixing seat 2341, and the second nut fixing seat 2341 is fixedly connected to the transmission support plate 2310.

Specifically, the second trapezoidal screw 2470 passes through the second bearing seat 2211 and is rotatably coupled to it, where the second bearing seat 2211 is fixedly connected to the frame 2210.

In the present embodiments, the third trapezoidal screw 2351 belongs to the trapezoidal screw unit 2350 which further includes two third bearing seats 2352 fixed to the transmission support plate 2310, with the third trapezoidal screw 2351 being rotatably connected to the two third bearing seats 2352 at both ends.

The second adapter transmission assembly 2300 further includes a dual bearing seat assembly 2360 including a bearing seat body 2361 fixed to the transmission support plate 2310, where a plurality of bearing caps 2362 are detachably connected to the bearing seat body 2361 via fifth column head screws 2363, each bearing cap 2362 forming a bearing space together with the bearing seat body 2361, where a first rolling bearing 2364 is installed in the bearing space, and the second rotating shaft is fixedly coupled to the inner ring of the first rolling bearing 2364, so that the second rotating shaft is rotatably connected to the dual bearing seat assembly 2360.

Specifically, a reinforcing rib 2380 for improving structural strength is further connected between the slider fixing plate 2311 and the transmission support plate 2310.

In the prior art, the catheter adapter transmission assembly employs an electric cylinder for driving, with a synchronous belt being provided for transmission within the transmission chain. However, this design suffers from poor controllability, low transmission efficiency and challenges in manufacturability, thus it is difficult to meet the requirements for speed control and position control.

In the present embodiments, the first adapter transmission assembly 2200 has a first transmission module including a plurality of first transmission structures, each including a first transmission shaft 2242 rotatable around the adjustment direction, with respective third cross slider couplings 2250 being coaxially fixed to both ends of the first transmission shaft 2242, where one end of the first transmission shaft 2242 is coaxially fixed to one input end connection assembly 2270, and the other end is in transmission connection to one first adapter output assembly via a first bevel gear swivel 2233, where the first adapter assembly 8700 is in transmission-engagement with the output ends of all the first adapter output assemblies.

The above structural design establishes transmission connection between the axial end fixing assembly 2260 and the first adapter output assembly, which enables the power cabin 1000 to drive the first transmission module, thus ensuring that the first adapter assembly 8700 can complete the predetermined motions.

Specifically, there are three first transmission structures, and the first adapter output assembly includes one long shaft output assembly 2280 for first adapter assembly and two short shaft output assemblies 2290 for first adapter assembly. The first transmission module includes three first transmission shafts 2242 and two three-bearing supports 2241 arranged oppositely, and one end of each first transmission shaft 2242 is rotatably connected to one three-bearing support 2241 to rotate around its own axis. All the above-mentioned first transmission shafts 2242 and all the three-bearing supports 2241 form the second transmission unit 2240 for first adapter assembly.

The torque of the drive motor 1310 is transmitted to one of the third cross slider couplings 2250 via the axial end fixing assembly 2260, and then to the second transmission unit 2240 for first adapter assembly, and then to the first adapter assembly 8700 installed on the first transmission unit 2230 for first adapter assembly via the other third cross slider coupling 2250 and the first transmission unit 2230 for first adapter assembly to achieve torque transmission. The third cross slider couplings 2250 are used to compensate for the accumulated tolerance caused during the assembly of parts.

Exemplarily, the second adapter transmission assembly 2300 has a second transmission module including a plurality of second transmission structures, each including a second transmission shaft rotatable around the adjustment direction, where one end of the second transmission shaft is coaxially fixed to one input end connection assembly 2270 via one telescopic universal coupling 2264 and one second cross slider coupling 2265 in sequence, and the other end is in transmission connection to one second adapter output assembly 2330 via a second bevel gear swivel 2370, where the second adapter assembly 8800 is in transmission-engagement with the output ends of all the second adapter output assemblies 2330.

The above structural design establishes transmission connection between the axial end fixing assembly 2260 and the second adapter output assemblies 2330, which enables the power cabin 1000 to drive the second transmission module, thus ensuring that the second adapter assembly 8800 can complete the predetermined motions.

The torque of the drive motor 1310 is transmitted to the second cross slider coupling 2265 via the axial end fixing assembly 2260, and then to the telescopic universal coupling 2264, and then to the second adapter output assembly 2330 via the second transmission shaft, thereby achieving torque transmission.

In the present embodiments, the third adapter transmission assembly 2400 has a third transmission module including a plurality of third transmission structures, each including a ball spline assembly 2440 rotatable around the adjustment direction, where the ball spline assembly 2440 includes a ball spline outer shaft 2442 and a ball spline inner shaft 2263 in transmission engagement, the ball spline inner shaft 2263 being insertable into the ball spline outer shaft 2442 and coaxially fixed to one input end connection assembly 2270 via the universal coupling 2262, the ball spline outer shaft 2442 being in transmission connection to a third adapter output assembly 2430 via the third bevel gear swivel 2450, where the third adapter assembly 8900 is in transmission-engagement with the output ends of all the third adapter output assemblies 2430.

The above structural design establishes transmission connection between the axial end fixing assembly 2260 and the third adapter output assemblies 2430, which enables the power cabin 1000 to drive the third transmission module, thereby ensuring that the third adapter assembly 8900 can complete the predetermined motions.

The torque of the motor torque is transmitted to the universal coupling 2262 via the axial end fixing assembly 2260, and then to the ball spline inner shaft 2263, and the torque is transmitted to the ball spline outer shaft 2442 via the ball spline body 2441, and then to the third adapter output assembly 2430 via the third bevel gear swivel 2450, thereby achieving torque transmission.

In summary, the first adapter transmission assembly 2200, the second adapter transmission assembly 2300 and the third adapter transmission assembly 2400 are all driven by motors, thus enabling good controllability, and can output speed, position and even force as needed; in addition, the above structure is highly flexible, which enables replacement with different adapter transmission assemblies as needed for the transmission cabin 2000, thereby meeting different surgical technique requirements.

In the present embodiments, thirteen input-end connection assemblies 2270 are connected to the shaft-end fixing assembly 2260, which are in turn connected to five universal couplings 2262, three telescopic universal couplings 2264 and five third cross-slider couplings 2250 respectively.

Further, the input-end connection assembly 2270 includes an input-end connector shaft 2273, two first flanged bearings 2271, a first elastic retaining ring 2272, a first adapter assembly connection flange 2274, a first spring 2275 and two first column head screws 2276. Each first flanged bearing 2271 has an inner ring fitted with the input-end connector shaft 2273, and an outer ring fitted with the fixing end plate 2261. The first flanged bearing 2271 on the right side is axially positioned via the shoulder on the input-end connector shaft 2273. The shoulder on 273 realizes axial positioning, and the first flanged bearing 2271 on the left side is axially positioned via the first elastic retaining ring 2272. The first spring 2275 is located in the hole on the right side of the input connector shaft 2273. The first adapter assembly connection flange 2274 is installed on the right side of the first spring 2275, and is secured by the first column head screw 2276. When axially pressed, the first adapter assembly connection flange 2274 can be axially displaced under the elastic force of the first spring 2275. In this way, transmission engagement can be achieved without adding additional couplings, thereby facilitating the assembly and disassembly of the input end connection assembly 2270. Specifically, the first flanged bearing 2271 is a flanged deep groove ball bearing, and the first column head screw 2276 is an internal hexagon column head screw.

Exemplarily, the long shaft output assembly 2280 for first adapter assembly includes a second adapter connection flange 2281, two second flanged bearings 2282, a second elastic retaining ring 2283, a long connector shaft 2284, a second spring 2285, two second column screws 2286 and a long connector bearing seat 2287. The second flanged bearing 2282 has an outer ring fitted with the long connector bearing seat 2287 that is fixed relative to the frame 2210.

In the present embodiments, the short shaft output assembly 2290 for first adapter assembly includes a third adapter connection flange 2291, a third flanged bearing 2292, a third elastic retaining ring 2293, a short connector shaft 2294, a third spring 2295, a third column screw 2296 and a short connector bearing seat 2297. The third flanged bearing 2292 has an outer ring fitted with the short connector bearing seat 2297 that is fixed relative to the frame 2210.

In the present embodiments, the third adapter output assembly 2430 includes a fifth adapter connection flange 2431, two fifth flanged bearings 2432, a fifth elastic retaining ring 2433, a third adapter connector shaft 2434, a fifth spring 2435 and two fifth column head screws 2436. The fifth flanged bearing 2432 has an outer ring fitted with the third adapter mounting cover 2420 that is fixed relative to the slider connection plate 2410. Specifically, a second slider 2411 is provided at the bottom of the slider connection plate 2410, and is slidably engaged with the transmission support plate 2310; one end of the ball spline outer shaft 2442 away from the ball spline inner shaft 2263 is rotatably connected to the slider connection plate 2410 via the second rolling bearing 2412.

In the present embodiments, the second adapter output assembly 2330 includes a fourth adapter connection flange 2331, two fourth flanged bearings 2332, a fourth elastic retaining ring 2333, a second adapter connector shaft 2334, a fourth spring 2335, two fourth column screws 2336 and a middle adapter output bearing seat 2337. The fourth flanged bearing 2332 has an outer ring fitted with the middle adapter output bearing seat 2337, and the middle adapter output bearing seat 2337 is fixed relative to the second adapter mounting cover 2320.

In the present embodiments, one end of the first transmission shaft 2242 away from the axial end fixing assembly 2260 is rotatably connected to the first adapter assembly mounting plate 2231 via the axial end assembly 2220 for first adapter assembly. The axial end assembly 2220 for first adapter assembly includes an output end bearing seat 2221, an output end shaft body 2222, two sixth flanged bearings 2223, a sixth elastic retaining ring 2224 and an output end shaft key 2225. The output end bearing seat 2221 has an outer wall inserted through the first adapter assembly mounting plate 2231, and the sixth flanged bearing 2223 has an outer ring fitted with the output end bearing seat 2221. The output end shaft key 2225 is fixedly connected to the output end shaft body 2222 which is keyed to the first transmission shaft 2242 via the output end shaft key 2225.

The specific structures of the above components are generally similar, all featuring a rotational connection between the rotating shaft and the bearing seat via the flanged bearing. Moreover, the rotating shaft has a spring interposed between the connection flange and the connector shaft, thereby enabling the connection flange and the connector shaft to move close to or away from each other in the lengthwise direction. Due to space limitations, detailed descriptions of the specific structures of these components are omitted here.

Exemplarily, the transmission cabin 2000 further includes a bedside operation panel 2191 provided on the chassis assembly 2100, where the bedside operation panel 2191 is communicatively connected to the first adapter assembly 8700, the second adapter assembly 8800 and the third adapter assembly 8900 and configured to display parameter information of the first adapter assembly 8700, the second adapter assembly 8800 and the third adapter assembly 8900. Configuration of the bedside operation panel 2191 enables surgeons to interactively operate the device at the operating bed, thereby facilitating more convenient and efficient surgical operations.

Specifically, the chassis assembly 2100 further includes a handle 2190 for surgeons to hold, where the handle 2190 is fixedly connected to the bottom bracket 2110, with the bedside operation panel 2191 being located above the handle 2190.

The present embodiments also provide a surgical assistance device including a robotic arm, a first adapter assembly 8700, a second adapter assembly 8800, a third adapter assembly 8900 and the above-mentioned surgical execution apparatus, where the chassis assembly 2100 of the surgical execution apparatus is detachably connected to the robotic arm. Specifically, the chassis assembly 2100 further includes an L-shaped support 2180 fixedly connected to the right side of the bottom bracket 2110, where an end flange is provided at the end of the robotic arm, and detachably connected to the L-shaped support 2180.

The surgical assistance device enables refined improvements on the operation of the mitral valve repair instrument 8000 through the cooperation of the surgical execution apparatus and the adapter assemblies. The use of surgical assistance device to assist the completion of the operation is intended to improve the quality and efficiency of the operation, mitigate or even avoid the harm of radiation to the health of surgeons, and enables simpler and more convenient procedure, thereby ultimately benefiting a large number of medical workers and patients.

The transmission cabin 2000 includes a chassis assembly 2100 and a first adapter transmission assembly 2200, a second adapter transmission assembly 2300 and a third adapter transmission assembly 2400 that are movable relative to the chassis assembly 2100. The first adapter transmission assembly 2200 is equipped with a first adapter assembly 8700 for connecting to the outer catheter 8310, the second adapter transmission assembly 2300 is equipped with a second adapter assembly 8800 for connecting to the middle catheter 8320, and the third adapter transmission assembly 2400 is equipped with a third adapter assembly 8900 for connecting to the output end of the inner catheter 8330. The power cabin 1000 is in transmission connection to the transmission cabin 2000, and configured to drive the outer catheter 8310 through the first adapter assembly 8700, drive the middle catheter 8320 through the second adapter assembly 8800, and drive the inner catheter 8330 through the third adapter assembly 8900.

The surgical assistance device can assist in valve repair surgery by driving and controlling the mitral valve repair instrument 8000. The design of separately driving the outer catheter 8310, the middle catheter 8320 and the inner catheter 8330 can enhance the flexibility of motions of the mitral valve repair instrument 8000, thus facilitates refined operations of the mitral valve repair instrument 8000. When used by surgeons to complete valve repair surgery, the surgical assistance device further ensures the stability and accuracy of the procedure.

The transmission cabin 2000 is configured to be connected to the mitral valve repair instrument 8000 through the first adapter assembly 8700, the second adapter assembly 8800 and the third adapter assembly 8900. On the one hand, the above structural improvement enables the mitral valve repair instrument 8000 to be effectively connected and fixed to the transmission cabin 2000 through the adapter assemblies, so that the surgeons can quickly, conveniently and stably install the mitral valve repair instrument 8000 on the transmission cabin 2000 during the operation preparation stage, and after the operation, the surgeons can quickly remove the mitral valve repair instrument 8000 from the transmission cabin 2000. On the other hand, the adapters enable the power of each power output shaft inside the transmission cabin 2000 to be stably and reliably transferred to each operating handle, operating knob and operating pull rod on the mitral valve repair instrument 8000.

Specifically, the mitral valve repair instrument 8000 further includes a first driving handle 8400, a second driving handle 8500, a third driving handle 8600, a guide wire 8100 and a sheath 8200 located at the end of the guide wire 8100. The surgical assistance device further includes a first adapter assembly 8700, a second adapter assembly 8800, and a third adapter assembly 8900. The first driving handle 8400 is mounted on the first adapter assembly 8700 and is in transmission connection to the first adapter assembly 8700, where the first adapter assembly 8700 is mounted on the first adapter transmission assembly 2200 and the first driving handle 8400 is configured to drive the outer catheter 8310. The second driving handle 8500 is mounted on the second adapter assembly 8800 and is in transmission connection to the second adapter assembly 8800, where the second adapter assembly 8800 is mounted on the second adapter transmission assembly 2300 and the second driving handle 8500 is configured to drive the middle catheter 8320. The third driving handle 8600 is mounted on the third adapter assembly 8900 and is in transmission connection to the third adapter assembly 8900, where the third adapter assembly 8900 is mounted on the third adapter transmission assembly 2400 and the third driving handle 8600 is configured to drive the inner catheter 8330.

Figure 41:
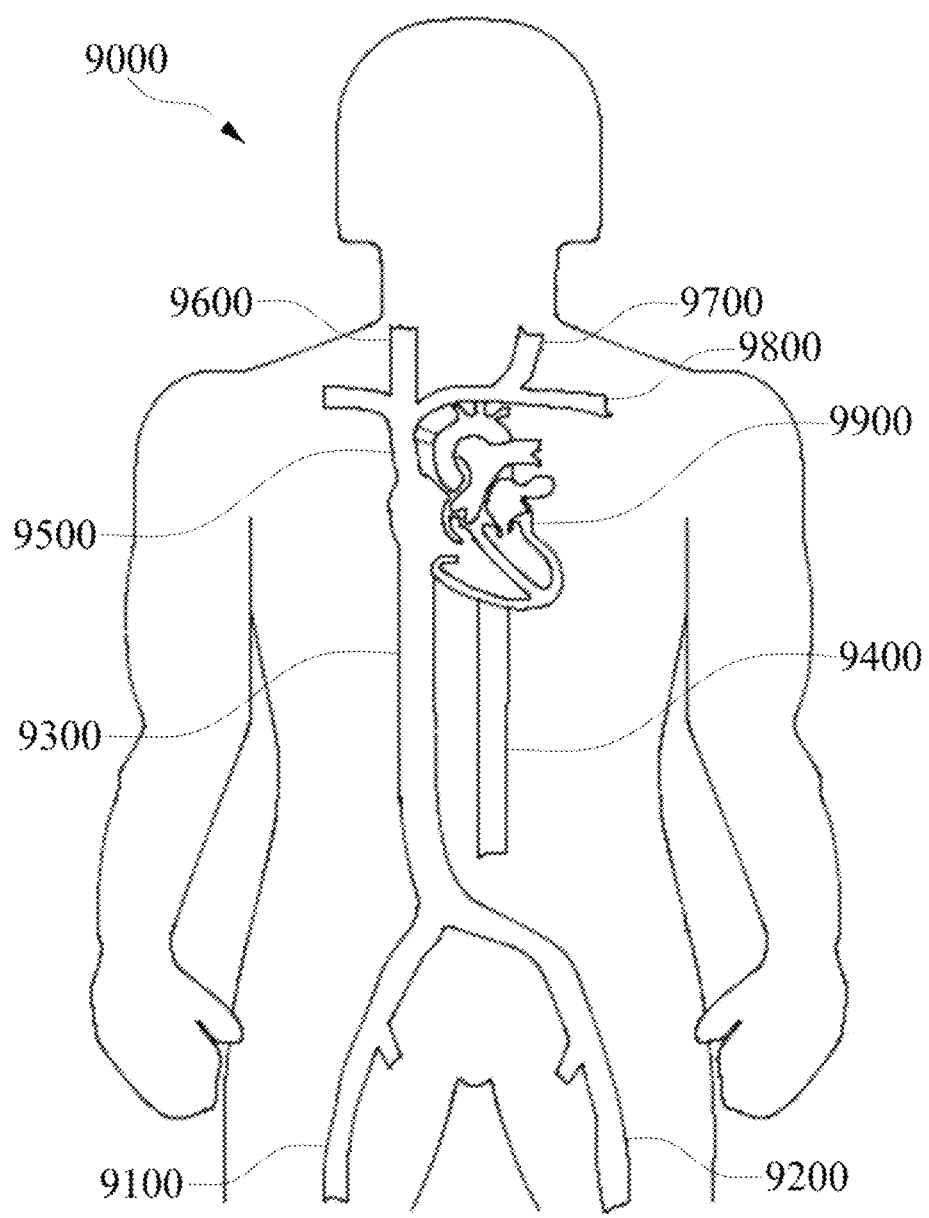
FIG. 41 is a cross-sectional view of a human body according to an embodiment of the present disclosure.
Figure 42:
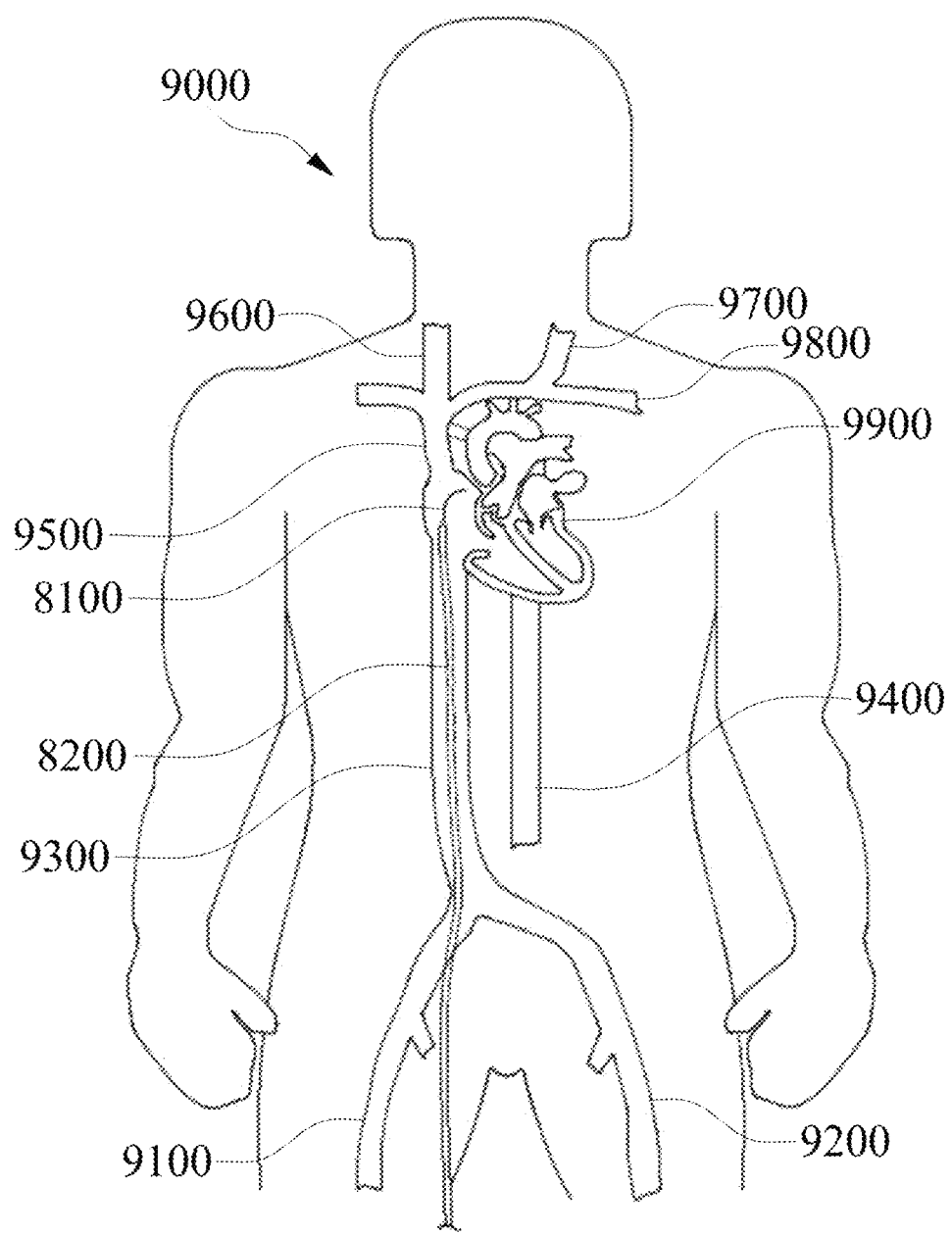
FIG. 42 is a cross-sectional view of a human body, a guide wire and a sheath according to an embodiment of the present disclosure.
Figure 43:
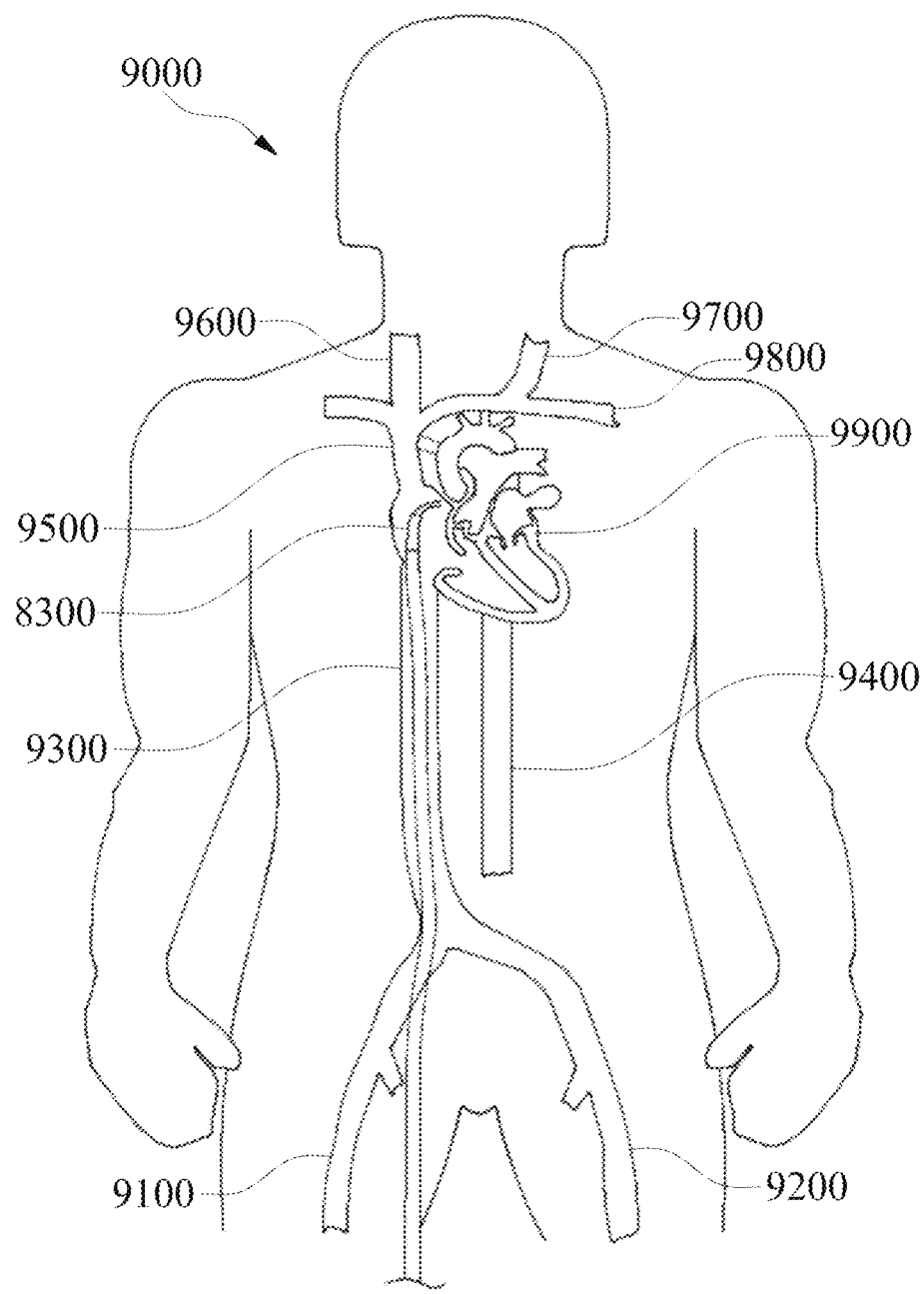
FIG. 43 is a cross-sectional view of a human body and a catheter assembly according to an embodiment of the present disclosure.
Figure 44:
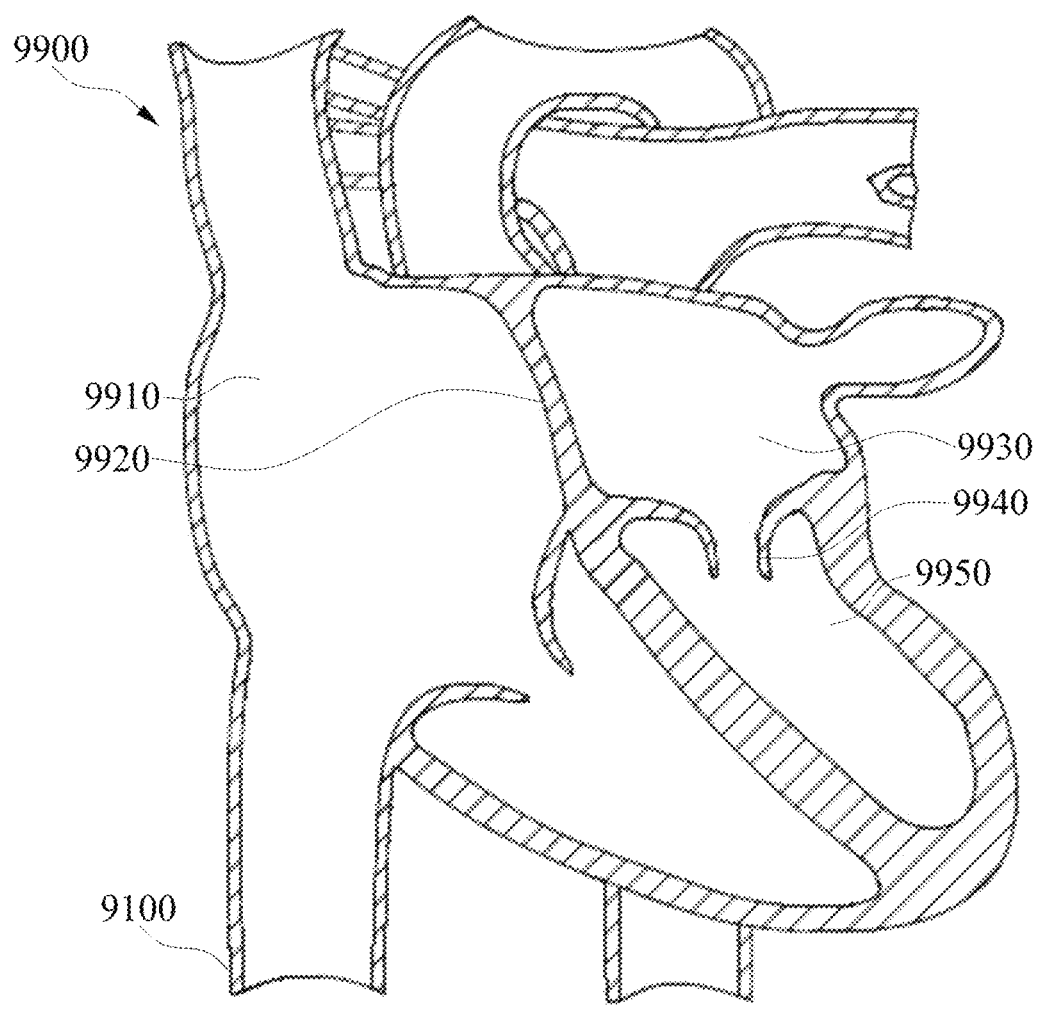
FIG. 44 is a cross-sectional view of a heart according to an embodiment of the present disclosure.
Figure 45:
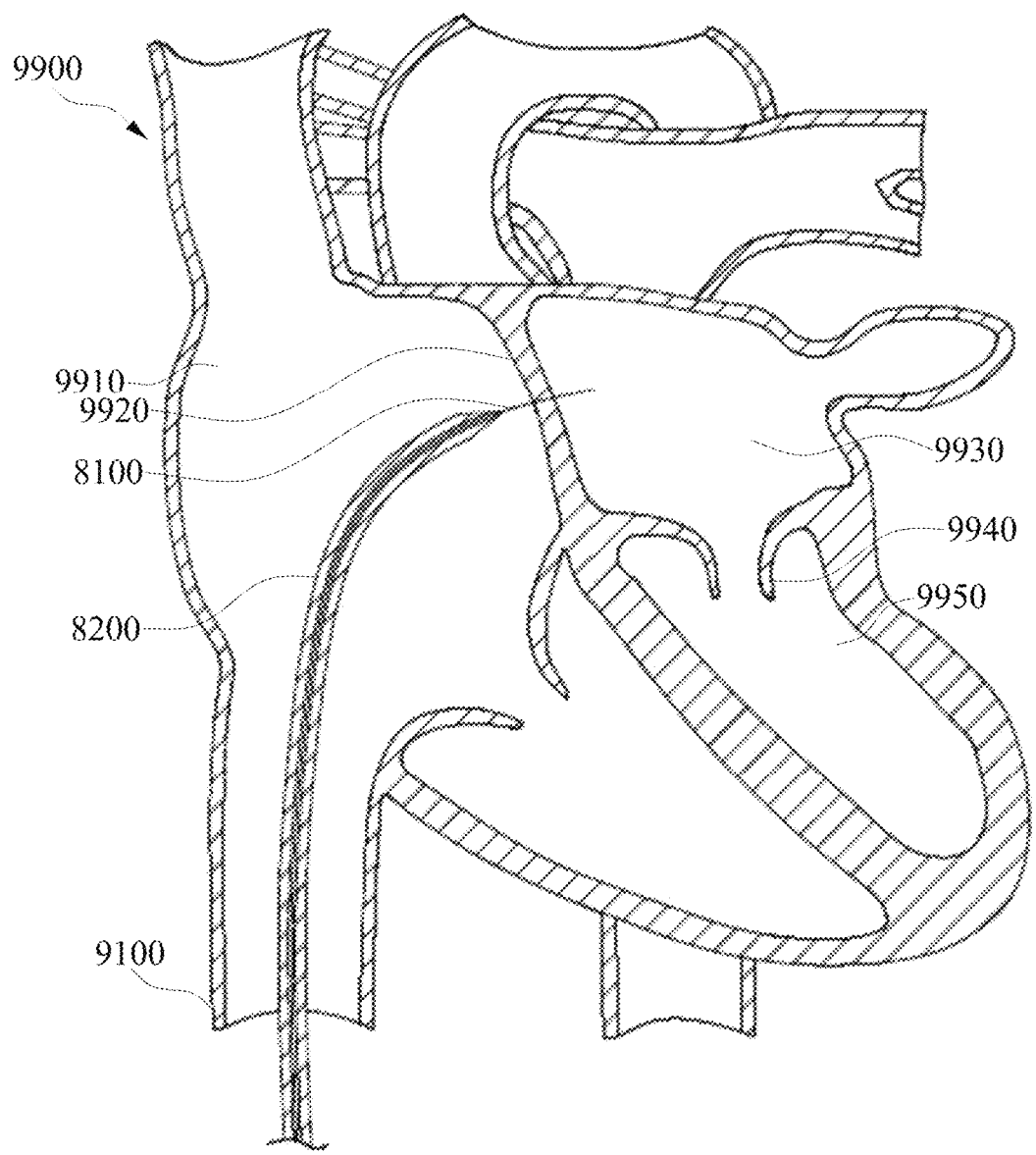
FIG. 45 is a cross-sectional view of a heart, a guide wire and a sheath according to an embodiment of the present disclosure.
Figure 46:
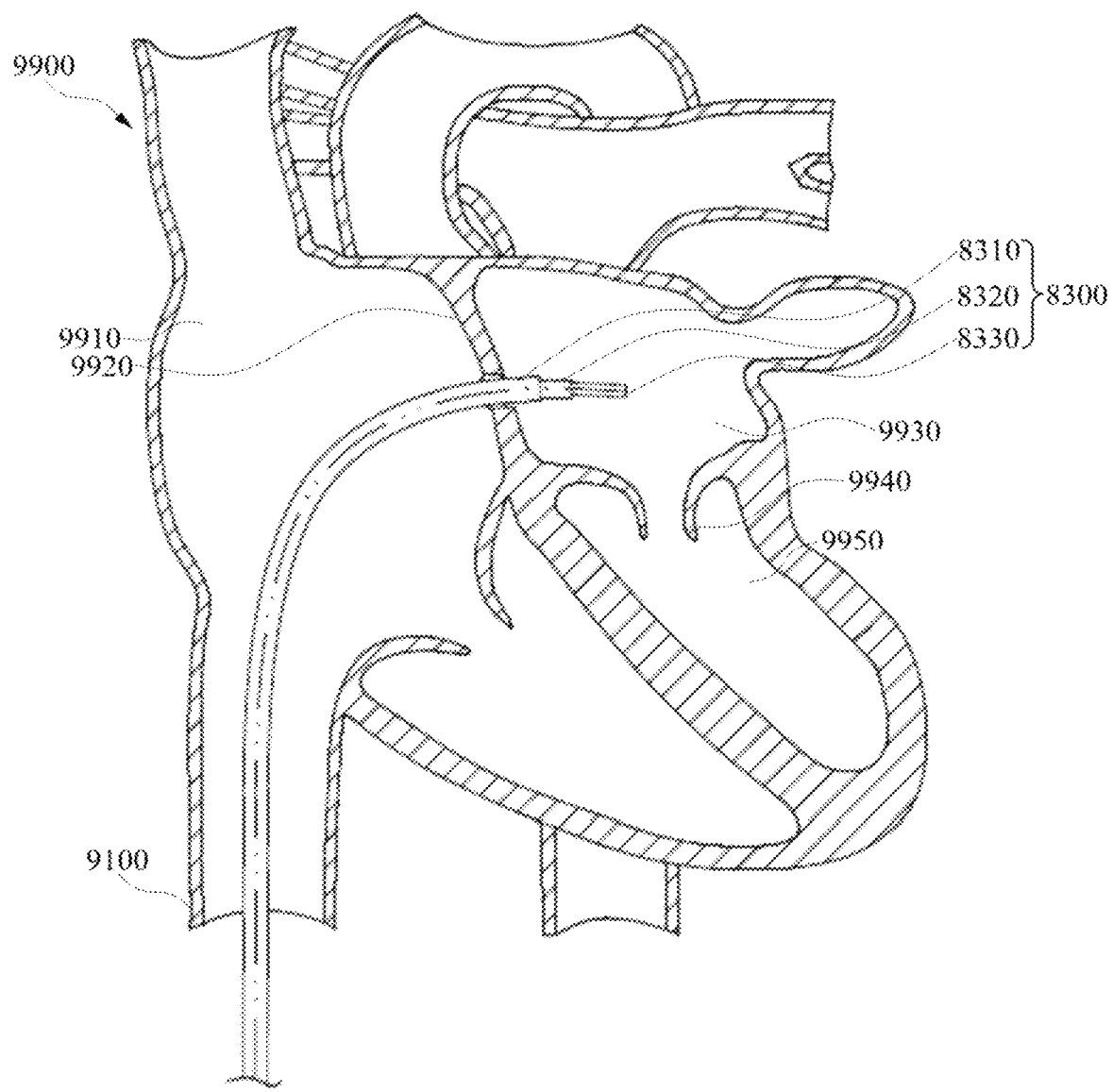
FIG. 46 is a cross-sectional view of a heart and a catheter assembly in the first state according to an embodiment of the present disclosure.
Figure 47:
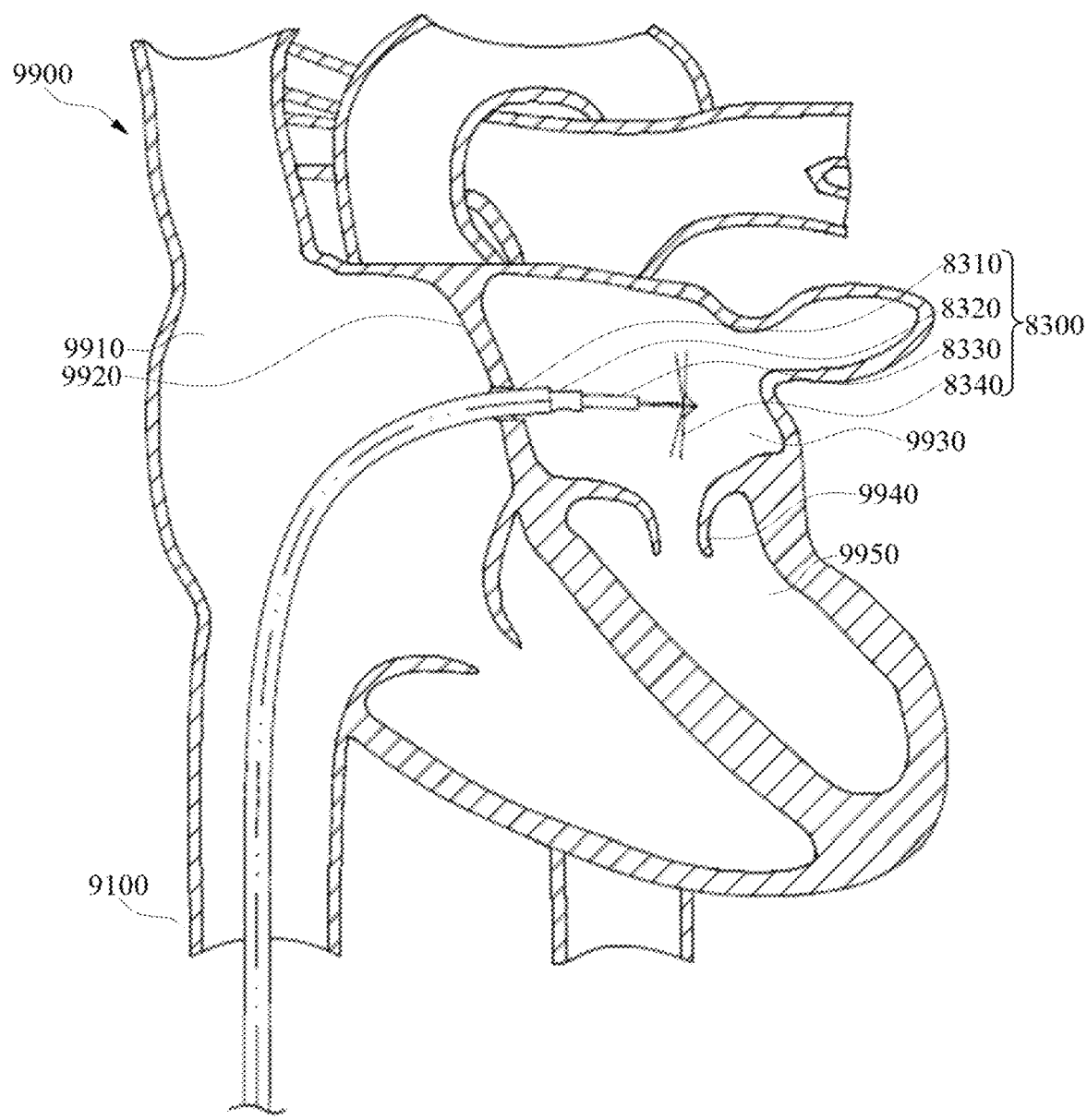
FIG. 47 is a cross-sectional view of a heart and a catheter assembly in the second state according to an embodiment of the present disclosure.
Figure 48:
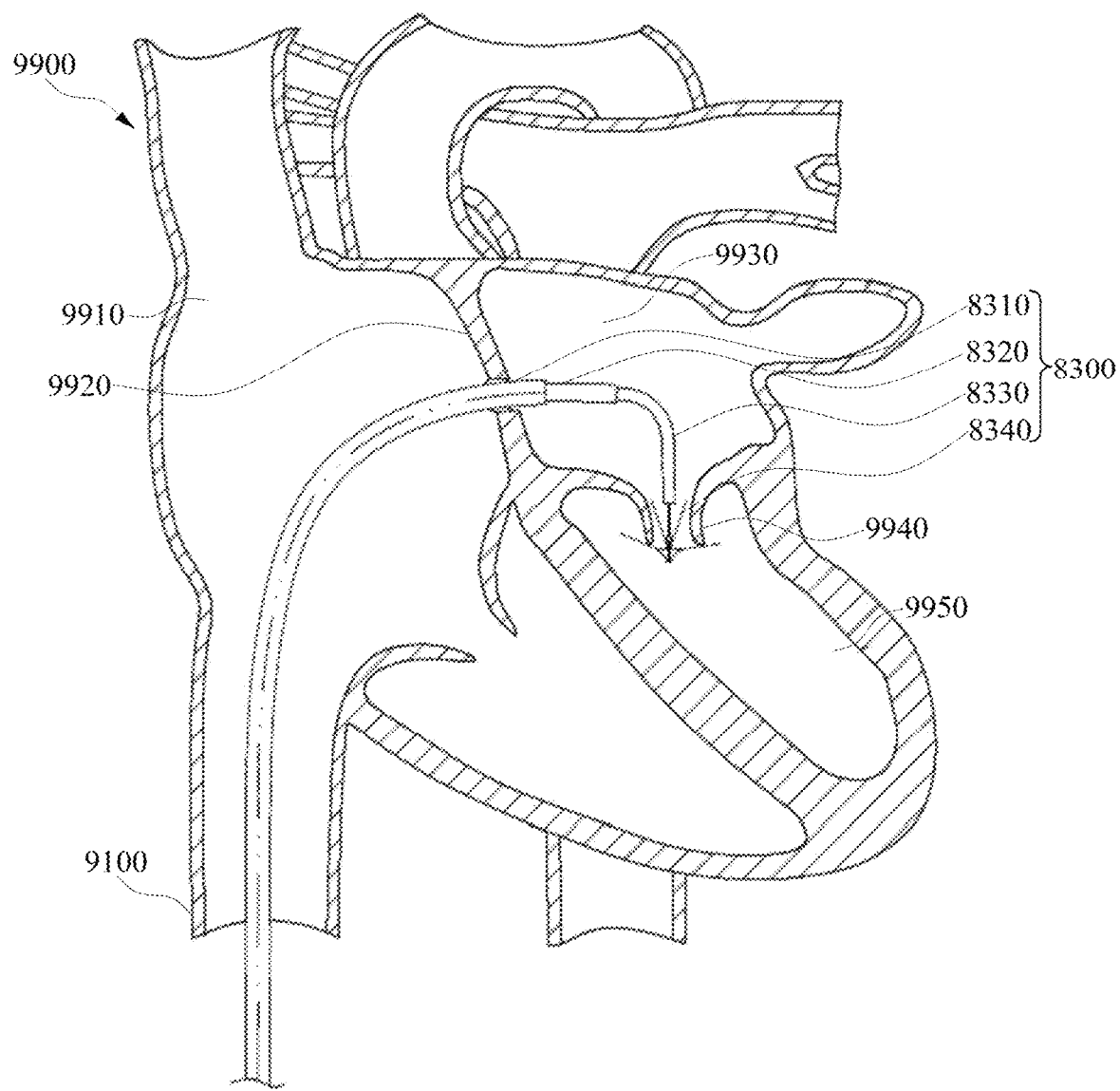
FIG. 48 is a cross-sectional view of a heart and a catheter assembly in the third state according to an embodiment of the present disclosure, where.

As shown in FIGS. 41 to 48, the human body 9000 has a right femoral vein 9100, a left femoral vein 9200, an inferior vena cava 9300, a descending aorta 9400, a superior vena cava 9500, a right jugular vein 9600, a left jugular vein 9700, a subclavian vein 9800, and a heart 9900. The heart 9900 has a right atrium 9910, an atrial septum 9920, a left atrium 9930, a mitral valve 9940, and a left ventricle 9950.

The present embodiment also provides a method for performing a valve repair surgery, which is applicable to the above-mentioned surgical assistance device, and includes: inserting the guide wire 8100 into the human body 9000, so that the sheath 8200 enters through the inferior vena cava 9300 into the right atrium 9910 of the heart 9900; puncturing the atrial septum 9920 using the sheath 8200; removing the guide wire 8100 and the sheath 8200, inserting the catheter assembly 8300 into the human body 9000, so that the catheter assembly 8300 enters through the inferior vena cava 9300 into the right atrium 9910 of the heart 9900 and the outer catheter 8310 passes through the atrial septum 9920 and at least partially extends into the left atrium 9930; controlling the outer catheter 8310, the middle catheter 8320 and the inner catheter 8330 to perform their own motions, so that the clip 8340 extends out of the middle catheter 8320 and switches to the unfolded state; controlling the outer catheter 8310, the middle catheter 8320 and the inner catheter 8330 to perform their own motions again, so that the clip 8340 penetrates the mitral valve 9940, and the mitral valve 9940 is clamped by the clamping part until the clip 8340 captures the mitral valve 9940. During the process of performing the valve repair surgery method, the catheter assembly 8300 is in the first state, the second state and the third state in sequence.

The valve repair surgery execution method enables smooth completion of the repair surgery for the mitral valve 9940 by sequentially introducing the guide wire 8100 and the mitral valve repair instrument 8000 into the human body 9000. The process is simple, reliable and has high operational stability, which facilitates simplification of the procedure of valve repair surgery and optimization of its steps.

The above steps can ensure the stability and accuracy of the surgery, thereby improving surgical efficiency and shortening the procedural time. The above method enables further improved working environment of surgeons, reduced physical demands on surgeons, and shortened learning curves for surgeons to master complex surgical techniques.

It is evident that the described embodiments of the present disclosure are merely illustrative examples provided to elucidate the present disclosure, and do not constitute limitations on the implementation of the present disclosure. A person of ordinary skill in the art can make various changes or modifications on the basis of the above description. It is neither necessary nor possible to exhaustively enumerate all possible implementations. Any modifications, equivalent substitutions, and improvements made within the spirit and principles of the disclosure are intended to be encompassed within the scope of the appended claims.

What is claimed is:

1. A surgical execution apparatus, comprising:
   a transmission cabin (2000) comprising a chassis assembly (2100) and further comprising a first adapter transmission assembly (2200), a second adapter transmission assembly (2300) and a third adapter transmission assembly (2400) that are movable relative to the chassis assembly (2100); and
   a power cabin (1000) in transmission connection to the transmission cabin (2000),
   wherein the first adapter transmission assembly (2200) is slidably attached to the chassis assembly (2100) to slide along an adjustment direction that is parallel to a lengthwise direction of the transmission cabin (2000), the second adapter transmission assembly (2300) is slidably attached to the first adapter transmission assembly (2200) to slide along the adjustment direction, and the third adapter transmission assembly (2400) is slidably attached to the second adapter transmission assembly (2300) to slide along the adjustment direction.

2. The surgical execution apparatus according to claim 1, wherein the power cabin (1000) comprises a motor assembly (1300) comprising an assembly frame plate (1320) and a plurality of drive motors (1310) mounted on the assembly frame plate (1320), with output ends of the drive motors (1310) extending through the assembly frame plate (1320); and the transmission cabin (2000) further comprises an axial end fixing assembly (2260) provided at one end of the first adapter transmission assembly (2200), the axial end fixing assembly (2260) comprising a fixing end plate (2261) and input end connection assemblies (2270) extending through and rotatably connected to the fixing end plate (2261), wherein the input end connection assemblies (2270) and the drive motors (1310) are equal in number, and each of the input end connection assemblies (2270) is coaxially and detachably connected to an output end of one of the drive motors (1310).

3. The surgical execution apparatus according to claim 2, wherein the chassis assembly (2100) comprises a bottom bracket (2110) and a guide rail connection plate (2130) slidably provided on the bottom bracket (2110), and the first adapter transmission assembly (2200) comprises a frame (2210), with the axial end fixing assembly (2260) being fixed to one end of the frame (2210), and the guide rail connection plate (2130) being fixed to the frame (2210).

4. The surgical execution apparatus according to claim 3, wherein a first trapezoidal nut (2123) is installed on the bottom bracket (2110), and a first trapezoidal screw (2132) is rotatably connected to the guide rail connection plate (2130) to rotate around the adjustment direction, the first trapezoidal nut (2123) being in transmission engagement with the first trapezoidal screw (2132); and/or
   the second adapter transmission assembly (2300) comprises a transmission support plate (2310) with a second trapezoidal nut (2342) being installed thereon, and a second trapezoidal screw (2470) is rotatably connected to the axial end fixing assembly (2260) to rotate around the adjustment direction, the second trapezoidal nut (2342) being in transmission engagement with the second trapezoidal screw (2470); and/or
   a third trapezoidal screw (2351) is rotatably connected to the transmission support plate (2310) to rotate around the adjustment direction, and the third adapter transmission assembly (2400) comprises a slider connection plate (2410) with a third trapezoidal nut (2460) being installed thereon, the third trapezoidal nut (2460) being in transmission engagement with the third trapezoidal screw (2351).

5. The surgical execution apparatus according to claim 4, wherein the first trapezoidal screw (2132) is coaxially fixed to one of the input end connection assemblies (2270) via one first cross slider coupling (2140) and one of second cross slider couplings (2265) in sequence; and/or
   the second trapezoidal screw (2470) is coaxially fixed to one of the input end connection assemblies (2270) via one of the second cross slider couplings (2265); and/or
   the third trapezoidal screw (2351) is coaxially fixed to one of the input end connection assemblies (2270) via one of telescopic universal couplings (2264) and one of the second cross slider couplings (2265) in sequence.

6. The surgical execution apparatus according to claim 3, wherein the first adapter transmission assembly (2200) further comprises a first transmission module comprising a plurality of first transmission structures, each comprising a first transmission shaft (2242) rotatable around the adjustment direction, with respective third cross slider couplings (2250) being coaxially fixed to both ends of the first transmission shaft (2242), wherein one end of the first transmission shaft (2242) is coaxially fixed to one of the input end connection assemblies (2270) and the other end is in transmission connection to one of first adapter output assemblies via a first bevel gear swivel (2233).

7. The surgical execution apparatus according to claim 3, wherein the second comprising a plurality of second transmission structures, each comprising a second transmission shaft rotatable around the adjustment direction, with one end of the second transmission shaft being coaxially fixed to one of the input end connection assemblies (2270) via one of telescopic universal couplings (2264) and one of second cross slider couplings (2265) in sequence, and the other end being in transmission connection to one of second adapter output assemblies (2330) via a second bevel gear swivel (2370).

8. The surgical execution apparatus according to claim 3, wherein the third adapter transmission assembly (2400) comprises a third transmission module comprising a plurality of third transmission structures, each comprising a ball spline assembly (2440) rotatable around the adjustment direction, wherein the ball spline assembly (2440) comprises a ball spline outer shaft (2442) and a ball spline inner shaft (2263) in transmission engagement, the ball spline inner shaft (2263) being insertable into the ball spline outer shaft (2442) and coaxially fixed to one of the input end connection assemblies (2270) via a universal coupling (2262), and the ball spline outer shaft (2442) being in transmission connection to one of third adapter output assemblies (2430) via a third bevel gear swivel (2450).

9. A surgical assistance device, comprising a robotic arm, a first adapter assembly, a second adapter assembly, a third adapter assembly and a surgical execution apparatus that is detachably connected to the robotic arm and comprises:
   a transmission cabin (2000) comprising a chassis assembly (2100) and further comprising a first adapter transmission assembly (2200), a second adapter transmission assembly (2300) and a third adapter transmission assembly (2400) that are movable relative to the chassis assembly (2100); and
   a power cabin (1000) in transmission connection to the transmission cabin (2000),
   wherein the first adapter transmission assembly (2200) is slidably attached to the chassis assembly (2100) to slide along an adjustment direction that is parallel to a lengthwise direction of the transmission cabin (2000), the second adapter transmission assembly (2300) is slidably attached to the first adapter transmission assembly (2200) to slide along the adjustment direction, and the third adapter transmission assembly (2400) is slidably attached to the second adapter transmission assembly (2300) to slide along the adjustment direction,
   wherein the first adapter transmission assembly (2200) comprises a first transmission module detachably connected to the first adapter assembly, the second detachably connected to the second adapter assembly, and the third adapter transmission assembly (2400) comprises a third transmission module detachably connected to the second adapter assembly; and
   the power cabin (1000) is configured to drive the first adapter assembly via the first transmission module, drive the second adapter assembly via the second transmission module, and drive the third adapter assembly via the third transmission module.

10. The surgical assistance device according to claim 9, wherein the transmission cabin (2000) further comprises an operation panel (2191) provided on the chassis assembly (2100), the operation panel (2191) being communicatively connected to the first adapter assembly, the second adapter assembly and the third adapter assembly, and configured to display parameter information of the first adapter assembly, the second adapter assembly and the third adapter assembly.

11. The surgical assistance device according to claim 9, wherein the power cabin (1000) comprises a motor assembly (1300) comprising an assembly frame plate (1320) and a plurality of drive motors (1310) mounted on the assembly frame plate (1320), with output ends of the drive motors (1310) extending through the assembly frame plate (1320); and the transmission cabin (2000) further comprises an axial end fixing assembly (2260) provided at one end of the first adapter transmission assembly (2200), the axial end fixing assembly (2260) comprising a fixing end plate (2261) and input end connection assemblies (2270) extending through and rotatably connected to the fixing end plate (2261), wherein the input end connection assemblies (2270) and the drive motors (1310) are equal in number, and each of the input end connection assemblies (2270) is coaxially and detachably connected to an output end of one of the drive motors (1310).

12. The surgical assistance device according to claim 11, wherein the chassis assembly (2100) comprises a bottom bracket (2110) and a guide rail connection plate (2130) slidably provided on the bottom bracket (2110), and the first adapter transmission assembly (2200) comprises a frame (2210), with the axial end fixing assembly (2260) being fixed to one end of the frame (2210), and the guide rail connection plate (2130) being fixed to the frame (2210).

13. The surgical assistance device according to claim 12, wherein a first trapezoidal nut (2123) is installed on the bottom bracket (2110), and a first trapezoidal screw (2132) is rotatably connected to the guide rail connection plate (2130) to rotate around the adjustment direction, the first trapezoidal nut (2123) being in transmission engagement with the first trapezoidal screw (2132); and/or
   the second adapter transmission assembly (2300) comprises a transmission support plate (2310) with a second trapezoidal nut (2342) being installed thereon, and a second trapezoidal screw (2470) is rotatably connected to the axial end fixing assembly (2260) to rotate around the adjustment direction, the second trapezoidal nut (2342) being in transmission engagement with the second trapezoidal screw (2470); and/or
   a third trapezoidal screw (2351) is rotatably connected to the transmission support plate (2310) to rotate around the adjustment direction, and the third adapter transmission assembly (2400) comprises a slider connection plate (2410) with a third trapezoidal nut (2460) being installed thereon, the third trapezoidal nut (2460) being in transmission engagement with the third trapezoidal screw (2351).

14. The surgical assistance device according to claim 13, wherein the first trapezoidal screw (2132) is coaxially fixed to one of the input end connection assemblies (2270) via one first cross slider coupling (2140) and one of second cross slider couplings (2265) in sequence; and/or
   the second trapezoidal screw (2470) is coaxially fixed to one of the input end connection assemblies (2270) via one of the second cross slider couplings (2265); and/or
   the third trapezoidal screw (2351) is coaxially fixed to one of the input end connection assemblies (2270) via one of telescopic universal couplings (2264) and one of the second cross slider couplings (2265) in sequence.

15. The surgical assistance device according to claim 12, wherein the first adapter transmission assembly (2200) further comprises a first transmission module comprising a plurality of first transmission structures, each comprising a first transmission shaft (2242) rotatable around the adjustment direction, with respective third cross slider couplings (2250) being coaxially fixed to both ends of the first transmission shaft (2242), wherein one end of the first transmission shaft (2242) is coaxially fixed to one of the input end connection assemblies (2270) and the other end is in transmission connection to one of first adapter output assemblies via a first bevel gear swivel (2233).

16. The surgical assistance device according to claim 12, wherein the second comprising a plurality of second transmission structures, each comprising a second transmission shaft rotatable around the adjustment direction, with one end of the second transmission shaft being coaxially fixed to one of the input end connection assemblies (2270) via one of telescopic universal couplings (2264) and one of second cross slider couplings (2265) in sequence, and the other end being in transmission connection to one of second adapter output assemblies (2330) via a second bevel gear swivel (2370).

17. The surgical assistance device according to claim 12, wherein the third adapter transmission assembly (2400) comprises a third transmission module comprising a plurality of third transmission structures, each comprising a ball spline assembly (2440) rotatable around the adjustment direction, wherein the ball spline assembly (2440) comprises a ball spline outer shaft (2442) and a ball spline inner shaft (2263) in transmission engagement, the ball spline inner shaft (2263) being insertable into the ball spline outer shaft (2442) and coaxially fixed to one of the input end connection assemblies (2270) via a universal coupling (2262), and the ball spline outer shaft (2442) being in transmission connection to one of third adapter output assemblies (2430) via a third bevel gear swivel (2450).

\* \* \* \* \*